United States Patent [19]

Hertel et al.

[11] Patent Number: 5,644,043

[45] Date of Patent: Jul. 1, 1997

[54] 2',3'-DIDEOXY-2',2'-DIFLUORONUCLEOSIDES AND INTERMEDIATES

[75] Inventors: Larry W. Hertel; Julian S. Kroin, both of Indianapolis, Ind.

[73] Assignee: Eli Lilly and Company, Indianapolis, Ind.

[21] Appl. No.: 173,256

[22] Filed: Dec. 27, 1993

Related U.S. Application Data

[63] Continuation of Ser. No. 964,121, Oct. 21, 1992, abandoned, which is a continuation of Ser. No. 394,382, Aug. 15, 1989, abandoned, which is a continuation-in-part of Ser. No. 295,321, Jan. 11, 1989, abandoned, which is a continuation-in-part of Ser. No. 156,116, Feb. 16, 1988, abandoned.

[51] Int. Cl.$^6$ .............................. C07H 15/00; C07H 19/00
[52] U.S. Cl. .................... 536/18.4; 536/4.1; 536/27.14; 536/27.21; 536/27.6; 536/27.61; 536/27.8; 536/27.81; 536/28.1; 536/28.2; 536/28.3; 536/28.4; 536/28.52; 536/28.54
[58] Field of Search ..................... 536/4.1, 18.4, 536/28.1, 28.5, 28.2, 28.3, 28.4, 28.52, 28.54, 27.21, 27.6, 27.61, 27, 27.8, 27.81, 27.14

[56] References Cited

U.S. PATENT DOCUMENTS

| | | | |
|---|---|---|---|
| 4,145,531 | 3/1979 | Eckstein et al. | 536/26 |
| 4,321,366 | 3/1982 | Bobek et al. | 536/122 |
| 4,526,988 | 7/1985 | Hertel | 549/313 |
| 4,681,873 | 7/1987 | McNamara et al. | 514/50 |
| 4,692,434 | 9/1987 | Hertel | 514/49 |
| 4,808,614 | 2/1989 | Hertel et al. | 514/45 |
| 4,880,782 | 11/1989 | Eckstein et al. | 514/46 |
| 4,908,440 | 3/1990 | Sterzicki et al. | 536/28.2 |

FOREIGN PATENT DOCUMENTS

| | | | |
|---|---|---|---|
| 184365 | 6/1986 | European Pat. Off. | C07H 19/06 |
| 211354 | 2/1987 | European Pat. Off. | C07H 10/073 |
| WO88/07861 | 10/1988 | WIPO. | |

OTHER PUBLICATIONS

New England Journal of Medicine 316:557–564 (Feb. 26, 1987) Yarchean et al.

Herdewijn et al., "Synth . . . Analysis", J. Med. Chem, vol. 30, pp. 2131–2137 (1987).

Bergstrom et al., "Abstract presented at Spring 1983 ACS Meeting" in Seattle, WA.

C. A. Abstract 109:222451f (1989).

Wright and Taylor, *Carbohydrate Res.* 6, 347–54, (1968).

Jarvi et al., Poster Session, 8th International Round Table Meeting on Nucleosides, Nurcleotides and their Biological Applications, Orange Beach, Ala., Oct. 2–5, 1988.

Sweeney et al, *Cancer Research,* 38, 2806–2891 (1978).

Miller et al., *J. Med. Chem.,*20(3), 409–413 (1977).

*Physician's Desk Reference,* pp. 2014–2017 (1984).

Goodman and Gilman's, *The Pharmacological Basis of Therapeutics,* 6th Ed., Melon Publishing Co., Inc., pp. 1280–1281 (1980).

*Primary Examiner*—James O. Wilson
*Attorney, Agent, or Firm*—Margaret M. Brumm; Robert D. Titus; Douglas J. Taylor

[57] ABSTRACT

This invention provides 2',3'-dideoxy-2',2'-difluoronucleosides of the structure

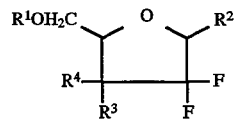

wherein $R^1$–$R^4$ are defined in the specification. These compounds have been shown to be useful for treating a variety of vital infections in experimental animals as well as having antineoplastic activity against various mouse tumors.

5 Claims, No Drawings

2',3'-DIDEOXY-2',2'-DIFLUORONUCLEOSIDES AND INTERMEDIATES

CROSS-REFERENCE

This application is continuation of application Ser. No. 07/964,121, filed Oct. 21, 1994, now abandoned which is a continuation of application Ser. No. 07/394,382, filed Aug. 15, 1989, now abandoned which is a continuation-in-part of application Ser. No. 07/295,321, filed Jan. 11, 1989, now abandoned, which is a continuation-in-part of application Ser. No. 07/156,116, filed Feb. 16, 1988, now abandoned.

BACKGROUND OF THE INVENTION

While the treatment of cancer was once considered impossible, great strides have been made during the past ten years in controlling the ravages of this often fatal disease. Several drugs which contribute to the increasing survival rate of patients diagnosed as having one of several types of cancer are now routinely used clinically. The most commonly employed antitumor drugs include methotrexate, doxorubicin, cytarabine and the vinca alkaloids such as vincristine. However, research continues to develop more effective compounds with improved efficacy and greater safety for subjects under treatment for cancer.

The search for chemical compounds with oncolytic activity has revealed a class of 2'-deoxy-2',2'-difluoronucleosides which exhibit excellent activity against a variety of tumors, both solid and non-solid types, as disclosed in EPO Application 85308547.0. These compounds, and their use as antiviral agents, are also disclosed in U.S. Pat. Nos. 4,526,988 and 4,692,434.

The present invention provides a new class of 2',3'-dideoxy-2',2'-difluoronucleosides for use as both oncolytic and antiviral agents. Novel intermediates used to synthesize these compounds are also provided.

SUMMARY OF THE INVENTION

The present invention provides a new class of 2',3'-dideoxy-2',2'-difluoronucleosides useful for treating susceptible neoplasms in mammals and for treating viral infections in mammals. More specifically, the present invention relates to a compound of the formula

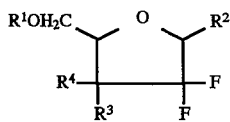

wherein:

$R^1$ is hydrogen, $C_1$–$C_4$ alkyl or

$R^2$ is a base defined by one of the formulae

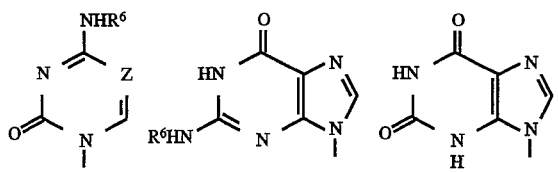

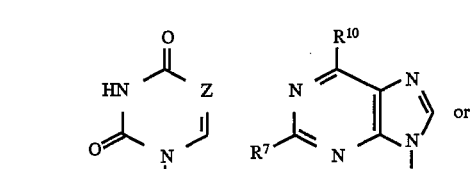

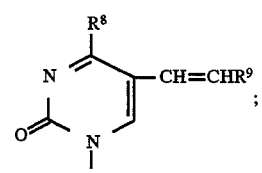

$R^3$ is hydrogen, amino, azido or fluoro;
$R^4$ is hydrogen or fluoro;
each $R^5$ independently is hydrogen or $C_1$–$C_4$ alkyl;
$R^6$ is hydrogen, $C_1$–$C_4$ alkyl or

$R^7$ is hydrogen, $C_1$–$C_4$ alkyl, $C_1$–$C_4$ haloalkyl, amino, bromo, fluoro, chloro or iodo;
$R^8$ is hydroxy or amino;
$R^9$ is hydrogen, bromo, chloro or iodo;
$R^{10}$ is —$NHR^6$, bromo, chloro, hydroxy, fluoro or iodo;
Z is N or C—$R^7$; or
a pharmaceutically-acceptable salt thereof; with the proviso that when $R^4$ is fluoro, $R^3$ is other than amino or azido.

The present invention also provides a pharmaceutical formulation comprising a compound of Formula I and a pharmaceutically acceptable carrier, diluent or excipient therefor.

Further embodiments of the invention are methods for treating susceptible neoplasms in mammals and for treating viral infections in mammals employing a compound of Formula I.

The present invention further provides an intermediate of the formula

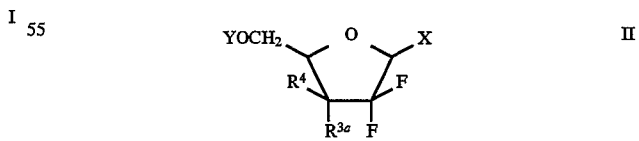

wherein:

X is hydroxy, a protected hydroxy, a leaving group or $R^2$;
Y is hydrogen or a hydroxy protecting group;
$R^{3a}$ is hydrogen, amino, azido, fluoro, hydroxy, a protected hydroxy or a leaving group;
$R^4$ is hydrogen or fluoro; With the following provisions:
a.) when $R^4$ is fluoro, $R^{3a}$ must be hydrogen or fluoro;

b.) when $R^{3a}$ is a leaving group, Y must be a hydroxy protecting group and X must be a protected hydroxy or a base;

c.) when X is a leaving group, Y must be a hydroxy protecting group and $R^{3a}$ must be other than hydroxy or a leaving group;

d.) when Y is hydrogen and X is a base or hydroxy, $R^{3a}$ must not be hydroxy;

e.) when $R^{3a}$ is hydroxy or a protected hydroxy then X must not be hydroxy;

f.) when Y is a hydroxy protecting group and $R^{3a}$ is a protected hydroxy then X must not be a leaving group.

DETAILED DESCRIPTION OF THE INVENTION

In the above formula, the term $C_1$–$C_4$ alkyl represents a straight or branched alkyl chain comprising from one to four carbon atoms. Typical $C_1$–$C_4$ alkyl groups include methyl, ethyl, n-propyl, isopropyl, n-butyl, isobutyl, sec-butyl and t-butyl.

Halo represents fluoro, chloro, bromo or iodo.

$C_1$–$C_4$ Haloalkyl represents a $C_1$–$C_4$ alkyl group having one or more halogen substituents. Typical $C_1$–$C_4$ haloalkyl groups include trifluoromethyl, 2,2,3,3-tetrafluoroethyl, 4,4,4-trifluorobutyl, 2-chloroethyl, 3-bromopropyl and the like.

The term "hydroxy protecting group", as used herein, represents that substituent which can be placed efficiently on a hydroxy group, and which can be removed easily when the reaction is complete. Suitable groups may be those described in standard textbooks, such as Chapter 3 of *Protective Groups in Organic Chemistry*, McOmie, Ed., Plenum Press, New York (1973); and Chapter 2 of *Protective Groups in Organic Synthesis*, Greene, John Wiley & Sons, New York (1981). Suitable hydroxy protecting groups commonly employed include formyl,

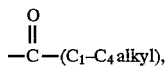

2-chloroacetyl, benzyl, diphenylmethyl, triphenylmethyl, 4-nitrobenzyl, phenoxycarbonyl, $C_1$–$C_4$ alkyl such as t-butyl, methoxymethyl, tetrahydropyranyl, allyl, tetrahydrothienyl, 2-methoxyethoxymethyl, methoxyacetyl, phenoxyacetyl, isobutyryl, ethoxycarbonyl, benzyloxycarbonyl, and optionally substituted benzoyl. The term "optionally substituted benzoyl" represents a benzoyl group with 0–2 substituents on its benzene ring. These substituents commonly are independently halogen, nitro, cyano, $C_1$–$C_4$ alkoxy, benzyloxy or $C_1$–$C_4$ alkyl.

Silyl hydroxy-protecting groups are particularly convenient because most of them are cleaved easily by contact with water or an alcohol. They are of the general formula Si(R', R", R'") where R', R", and R'" are independently methyl, ethyl, propyl, isopropyl, butyl, isobutyl, sec-butyl, t-butyl, or phenyl. Such groups may include especially t-butyldimethylsilyl, as well as isopropyldimethylsilyl, methyldiisopropylsilyl, trimethylsilyl or triisopropylsilyl.

The term "leaving group" represents a class of substituents which can be efficiently placed on a molecule and then displaced by a suitable nucleophile. Suitable substituents include those defined in standard textbooks such as *Advanced Organic Chemistry*, pages 310–316, Jerry March, John Wiley and Sons, New York (1985), and references cited therein. Suitable leaving groups include halogens, preferably bromine and chlorine. In the specific case of alcohols, the leaving group is defined as a substituent which can be placed efficiently on the hydroxyl group and then activates the entire moiety for displacement by a suitable nucleophile. These leaving groups include sulfonates such as p-bromobenzenesulfonate, p-nitrobenzenesulfonate, methanesulfonate, ammonioalkanesulfonates, alkylfluorosulfonates, 2,2,2-trifluoroethanesulfonate, nonafluorobutanesulfonate, and preferably p-toluenesulfonate or trifluoromethanesulfonate.

The structural drawings defining the compounds of the present invention do not indicate their stereochemistry. Compounds of all configurations are believed to be useful, and the stereochemistry of the compound is not to be construed as a limitation. The preferred compounds possess the configuration of naturally occurring ribose, for example,

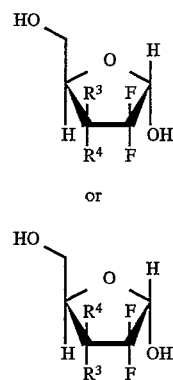

The configuration at the juncture between the carbohydrate and the base is preferably the β configuration as illustrated by the following

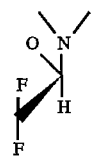

The following compounds further illustrate compounds contemplated within the scope of the present invention:

1-(2,4-dioxo-1H,3H-pyrimidin-1-yl)-2,3-dideoxy-2,2-difluororibose 1-(4-amino-5-chloro-2-oxo-1H-pyrimidin-1-yl)-2,3-dideoxy-2,2,3-trifluororibose 1-(4-amino-5-bromo-2-oxo-1H-pyrimidin-1-yl)-2,3-dideoxy-2,2-difluororibose 1-(4-amino-2-oxo-1H-pyrimidin-1-yl)-2,3-dideoxy-2,2-difluororibose 1-(4-amino-5-iodo-2-oxo-1H-pyrimidin-1-yl)-2,3-dideoxy-2,2-difluororibose 1-(4-amino-5-methyl-2-oxo-1H-pyrimidin-1-yl)-2,3-dideoxy-3-amino-2,2-difluororibose 1-(2-amino-6-oxo-1H,9H-purin-9-yl)-2,3-dideoxy-2,2-difluororibose 1-(6-amino-9H-purin-9-yl)-2,3-dideoxy-2,2-difluororibose 1-(4-amino-5-fluoro-2-oxo-1H-pyrimidin-1-yl)-2,3-dideoxy-2,2-difluororibose 1-(4-amino-5-chloro-2-oxo-1H-pyrimidin-1-yl)-2,3-dideoxy-3-azido-2,2-difluororibose 1-(4-amino-5-methyl-2-oxo-1H-pyrimidin-1-yl)-2,3-dideoxy-2,2,3,3-tetrafluoroxylose 1-(2-amino-6-oxo-1H,9H-purin-9-yl)-3-amino-2,3-dideoxy-2,2-difluororibose 1-(6-amino-9H-purin-9-yl)-3-azido-2,3-dideoxy-2,2-difluororibose 1-(6-bromo-2-chloro-9H-purin-9-yl)-2,3-dideoxy-2,2-difluororibose 1-(2-chloromethyl-6-iodo-9H-purin-9-yl)-2,3-dideoxy-2,2,3-trifluororibose or a pharmaceutically-acceptable salt thereof.

All of the above-described compounds of formula I are useful, of course, but certain compounds are preferred. Such preferred compounds are described by the following limitations. It will be understood that further preferred subclasses of compounds are to be obtained by combining the following limitations.

a. $R^3$ and $R^4$ are independently fluoro or hydrogen;
b. $R^3$ is amino or azido;
c. $R^6$ is hydrogen;
d. $R^5$ is alkyl;
e. $R^7$ is hydrogen or amino;
f. $R^{10}$ is —$NHR^6$;
g. $R^{10}$ is hydroxy.

All intermediates of formula II are useful but certain intermediates are preferred and are described by the following limitations. It will be understood that further preferred subclasses of intermediates are to be obtained by combining the following limitations.

a. X is a hydroxy protected with a silyl group, especially t-butyldimethylsilyl;
b. X is a leaving group, especially trifluoromethanesulfonyl;
c. X is a base;
d. $R^{3^a}$ is a hydroxy protected with a $C_1$–$C_4$ acyl or especially an optionally substituted benzoyl;
e. Y is a hydroxy protecting group selected from $C_1$–$C_4$ acyl or especially optionally substituted benzoyl;
f. $R^{3^a}$ is hydroxy or trifluoromethanesulfonyloxy;
g. $R^{3^a}$ is amino or azido;
h. $R^{3^a}$ and $R^4$ are independently fluoro or hydrogen.

As pointed out above, this invention includes the pharmaceutically acceptable salts of the compounds defined by the above formula. Since the compounds of this invention are basic in nature they react with any number of inorganic and organic acids to form pharmaceutically acceptable salts. Since the free amines of the invention are typically oils at room temperature or solids with low melting points, it is preferable to convert the free amines to their corresponding pharmaceutically acceptable salts, which are routinely solid at room temperature, for ease of handling and administration. Further, since salts of the compounds of the present invention are typically more water soluble than their corresponding free amines, these salts may be preferred in an effort to increase bioavailability of the active agent following administration. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonate, naphthalene-1-sulfonate, naphthalene-2-sulfonate, mandelate and the like salts. Preferred pharmaceutically acceptable salts include those formed with mineral acids such as hydrochloric acid and hydrobromic acid, and those formed with organic acids such as oxalic acid and maleic acid.

The nucleosides of the invention wherein both $R^3$ and $R^4$ are hydrogen are prepared by reacting a 2'-deoxy-2',2'-difluoronucleoside with a reagent capable of protecting any free hydroxy and amine substituents other than the hydroxy group at the 3'-position on the carbohydrate moiety. The protected compound is next reacted with a phenyl halothionocarbonate to provide the corresponding 3'-[(phenoxythioxomethyl)oxy]-2',2'-difluoronucleoside, which is treated with tributyltin hydride and an azobismethylpropionitrile. The resulting compound is finally deblocked to provide the corresponding 2',3'-dideoxy-2',2'-difluoronucleoside of the invention. This reaction is represented by the following scheme:

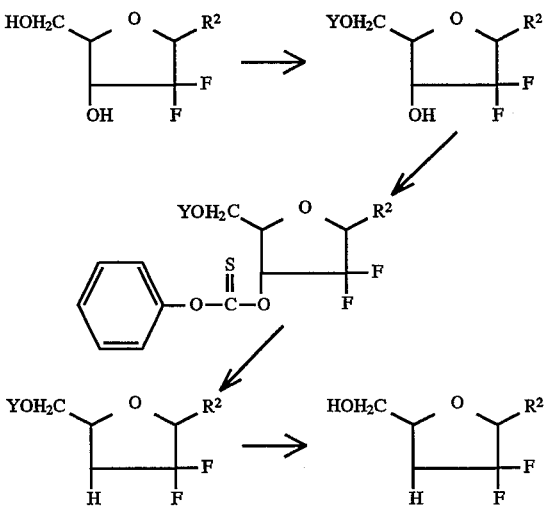

wherein $R^2$ is as defined above and Y is a hydroxy protecting group.

In the first step of the above-described reaction, the free hydroxy and amine substituents are protected without effect on the hydroxy group at the 3'-position of the carbohydrate moiety. According to this procedure, an equimolar or excess amount of a blocking agent such as pivaloyl chloride is added to a solution of the starting material in a suitable solvent such as pyridine. This reaction is conducted under standard acylation techniques in the presence of a small amount of acylation catalyst such as dimethylaminopyridine if desired. The product is isolated typically by concentrating the reaction mixture under vacuum and dissolving the resulting residue in a water immiscible organic solvent such as ethyl acetate or diethyl ether. The reaction mixture is washed with one and aqueous solutions and concentrated under vacuum to provide the desired compound which may be further purified by standard techniques or taken directly for use in the following reaction.

Alternatively, the starting compound may be reacted with a blocking agent such as benzoyl chloride which reacts with the 3'-position hydroxy as well as the other groups to be protected. This reaction is conducted under standard acylation conditions as described above. Then the 3'-benzoyl is deblocked to provide the corresponding compound of the invention wherein $R^3$ is amino and $R^4$ is hydrogen. The azide intermediate may be deblocked to provide a compound of the invention wherein $R^3$ is azido and $R^4$ is hydrogen. This reaction is represented by the following scheme:

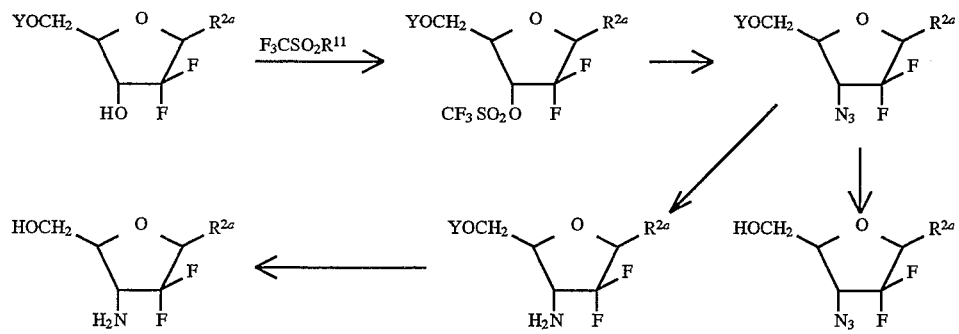

selectively removed either by reaction with hydrazine in a refluxing $C_1$–$C_4$ alcohol for from about 4 hours to two days, or by reaction with an alkaline metal alkoxide, particularly potassium t-butoxide, in an anhydrous solvent inert to the reaction conditions such as diethyl ether or especially tetrahydrofuran. The deprotection with an alkaline alkoxide is run at low temperature from about −20° C. to about −100° C. for a time ranging from about 15 minutes to about 3 hours. The reaction mixture requires neutralization with an acid, such as glacial acetic acid, before being allowed to warm to ambient temperature. The 3'-deprotected product can then be isolated as described above.

The hydroxy substituent at the 3'-position of the carbohydrate moiety is next converted to the 3'-phenoxythiocarbonyl ester according to procedures used previously on 2'-deoxyribonucleosides. See *Journal of American Chemical Society* 103, 932 (1981). According to this procedure, approximately an equimolar to slight excess of a phenyl halothionocarbonate is added to the starting material dissolved in a mutual solvent such as pyridine. A small amount of acylation catalyst such as dimethylaminopyridine may also be employed. The compound thus synthesized is reacted with tributyltin hydride in the presence of 2,2'-azobis[2-methylpropionitrile] in a suitable organic solvent such as toluene. The reaction is substantially complete when conducted at a temperature in the range of about 50° C. to about 150° C. for a period of about 30 minutes to about 12 hours. The product is isolated by concentrating the reaction mixture under vacuum and isolating the desired product according to standard procedures. The desired compound is finally synthesized by hydrolyzing the protecting groups in the presence of a concentrated base such as sodium hydroxide or any other alkali metal hydroxide reagent. The product is isolated according to standard procedures and purified by common techniques such as crystallization from common solvents or purification over solid supports such as silica gel or alumina, or by reverse phase $C_{18}$ chromatography, to provide the desired compound.

Compounds of the invention wherein $R^3$ is amino or azido and $R^4$ is hydrogen are prepared according to known procedures. The hydroxy substituent at the 3'-position of a blocked 2'-deoxy-2',2'-difluoroxylose as described above is functionalized with a trifluoromethanesulfonyl substituent. The resulting intermediate is reacted sequentially with a base, an azide reagent, catalytically hydrogenated and deblocked to provide the corresponding compound of the invention wherein $R^3$ is amino and $R^4$ is hydrogen. The azide intermediate may be deblocked to provide a compound of the invention wherein $R^3$ is azido and $R^4$ is hydrogen. This reaction is represented by the following scheme:

wherein $R^{2a}$ is a base as defined above or a protected hydroxy and $R^{11}$ is a good leaving group such as halogen, especially chloro.

The reaction of a blocked 2'-deoxy-2',2'-difluoronucleoside with the trifluoromethanesulfonyl reagent is carried out according to standard acylation conditions. The preferred trifluoromethanesulfonyl reagent will contain a halogen substituent, with trifluoromethanesulfonyl chloride being the especially preferred reagent. Typically an excess of such reagent is combined with a solution of the starting material dissolved in a mutual organic solvent. This reaction is complete within about 12 to 24 hours and it generally is conducted at a temperature from about 20° C. to about 100° C. The desired product may be isolated, if desired, by standard techniques.

The 3'-trifluorosulfonyloxy derivative thus prepared is next reacted with an equimolar to excess amount of an azide reagent for conversion to the appropriate 3'-azido derivative. Typical azide reagents include trimethylsilyl azide as well as the alkali metal azides such as lithium azide, sodium azide or potassium azide. The reaction is carried out in a suitable solvent under anhydrous conditions at a temperature in the range of about 100° C. to about −100° C. Suitable solvents include the aprotic solvents with N,N-dimethylformamide being preferred. The desired compound is preferably deblocked employing standard hydrolysis conditions in acid or base or converted to the 3'-amino derivative under standard catalytic hydrogenation conditions which is subsequently deblocked.

Compounds of the present invention wherein one of $R^3$ and $R^4$ is hydrogen and the other is fluoro are prepared by reacting a protected 2'-deoxy-2',2'-difluoronucleoside with diethylaminosulfur trifluoride (DAST) and deprotecting the resulting compound according to the following scheme:

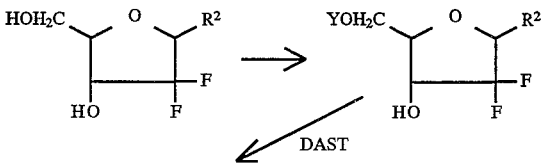

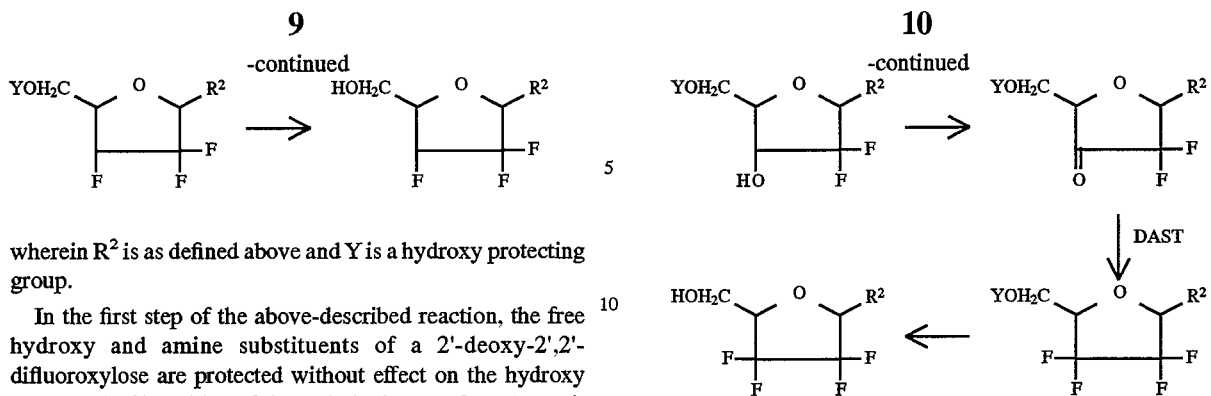

wherein R² is as defined above and Y is a hydroxy protecting group.

In the first step of the above-described reaction, the free hydroxy and amine substituents of a 2'-deoxy-2',2'-difluoroxylose are protected without effect on the hydroxy group at the 3'-position of the carbohydrate moiety. According to this procedure, an equimolar or excess amount of a blocking agent such as pivaloyl chloride is added to a solution of the starting material in a suitable solvent such as pyridine. This reaction is conducted under standard acylation techniques in the presence of a small amount of acylation catalyst such as dimethylaminopyridine if desired. The product is isolated typically by concentrating the reaction mixture under vacuum and dissolving the resulting residue in a water immiscible organic solvent such as ethyl acetate or diethyl ether. The reaction mixture is washed with one or more aqueous solutions and concentrated under vacuum to provide the desired compound which may be further purified by standard techniques or taken directly for use in the following reaction.

The hydroxy substituent at the 3'-position of the carbohydrate moiety is next converted to the fluoro substituent with DAST, a known fluorinating agent. See *Journal of Organic Chemistry* 40, 574 (1975) and *Tetrahedron Letters*, 573 (1977). According to this procedure, approximately an equimolar to slight excess of DAST is added to the starting material dissolved in a mutual solvent. The reaction is substantially complete when conducted at a temperature in the range of about 50° C. to about 150° C. for a period of about 30 minutes to about 12 hours. The product is isolated by concentrating the reaction mixture under vacuum and isolating the desired product according to standard procedures. The desired compound is finally synthesized by hydrolyzing the protecting groups in the presence of a concentrated base such as sodium hydroxide or any other alkali metal hydroxide reagent. The product is isolated according to standard procedures and purified by common techniques such as crystallization from common solvents or purification over solid supports such as silica gel or alumina, or by reverse phase C₁₈ chromatography, to provide the desired compound.

Compounds of the present invention wherein both R³ and R⁴ are fluoro are prepared by oxidizing the desired protected 2'-deoxy-2',2'-difluoronucleoside to provide the corresponding 3'-oxo-2',2'-difluoronucleoside which is treated with DAST and finally deprotected. This reaction may be represented by the following scheme:

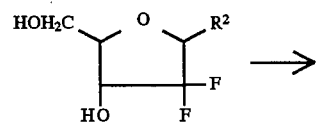

wherein R² is as defined above and Y is a hydroxy protecting group.

The protecting and deprotecting steps of the reaction, as well as the fluorination step with DAST, are all conducted according to the general conditions hereinbefore described. The process of oxidizing the 3'-hydroxy substituent to a 3'-oxo substituent is carried out according to standard conditions. Preferably, an equimolar to excess amount of dimethylsulfoxide-oxalyl chloride, also known as the Swern Reagent, is combined with the starting material in a suitable solvent such as methylene chloride according to Smith et al., *Synthesis* 567 (1981). The reaction is complete within about one hour to about 48 hours when conducted at a temperature in the range of about −80° C. to about 100° C. The product is isolated and purified, if desired, according to standard procedures.

Intermediates of the invention as defined by Formula II above may be prepared by procedures well known in the art or by procedures analogous to known processes and as hereinbefore provided. Intermediates of the invention wherein R³ and R⁴ are hydrogen or fluoro may be prepared by the reaction of D-glyceraldehyde ketonide and a C₁–C₄ alkyl-bromodifluoroacetate to provide an alkyl 3-dioxolanyl-2,2-difluoro-3-hydroxypropionate according to the procedure of Hertel in U.S. Pat. Nos. 4,526,988 and 4,692,434, herein incorporated by reference. Intermediates of the invention wherein R³ and R⁴ are both hydrogen are prepared by reacting the alkyl 3-dioxolanyl-2,2-difluoro-3-hydroxypropionate with a phenyl halothionocarbonate to provide the corresponding intermediate which is treated with tributyltin hydride and an azobismethylpropionitrile. The resulting alkyl 3-dioxolanyl-2,2-difluoropropionate is hydrolyzed under very mild conditions to provide the lactone form of the carbohydrate. Intermediates of the invention wherein one of R³ and R⁴ is hydrogen and the other is fluoro are prepared by fluorinating the alkyl 3-dioxolanyl-2,2-difluoro-3-hydroxypropionate to the alkyl 3-dioxolanyl-2,2,3-trifluoropropionate which is cyclized to the lactone form of the carbohydrate. For intermediates wherein R³ and R⁴ are both fluoro, the hydroxy substituent of the alkyl 3-dioxolanyl-2,2-difluoro-3-hydroxypropionate is oxidized to the keto derivative, and the resulting compound is converted to an alkyl 3-dioxolanyl-2,2,3,3-tetrafluoropropionate. This compound is cyclized to provide the lactone form of the carbohydrate. The carbohydrate intermediates of the invention are finally prepared by reducing the keto oxygen of the lactone. This reaction is set forth by the following scheme:

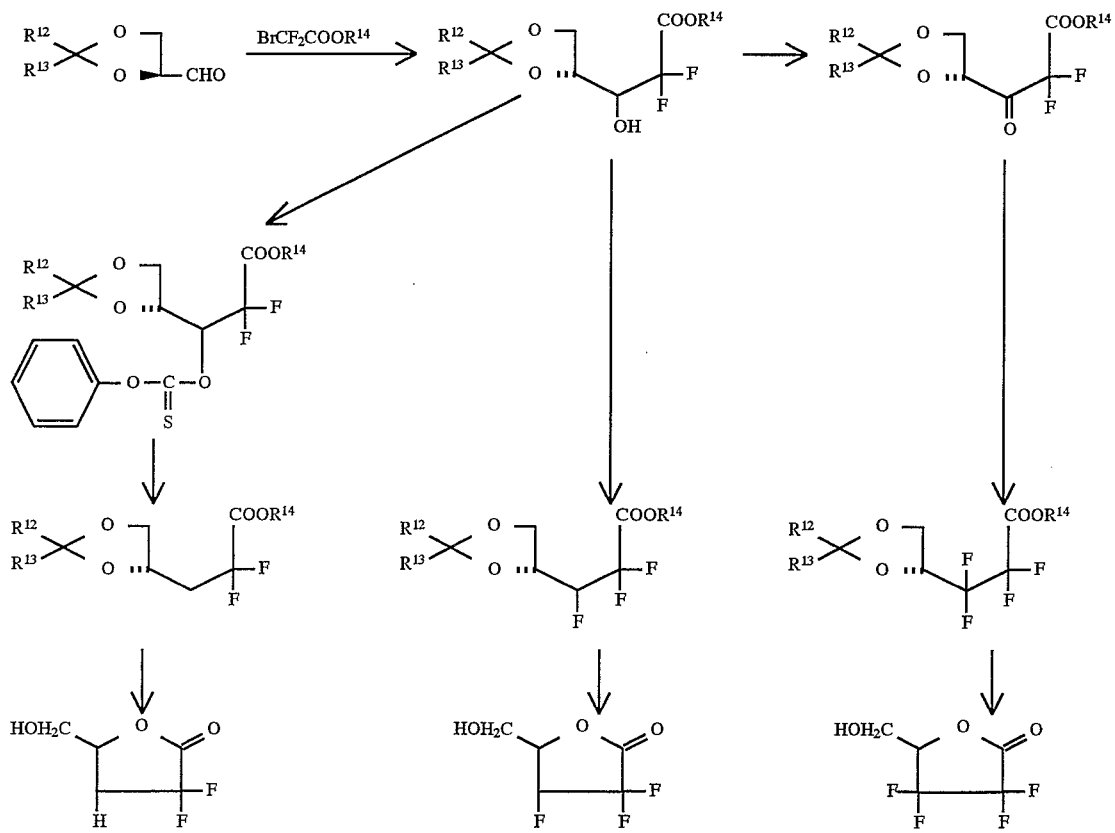

wherein $R^{12}$ and $R^{13}$ are independently $C_1$–$C_3$ alkyl and $R^{14}$ is $C_1$–$C_4$ alkyl.

Intermediates of the invention wherein $R^3$ is amino or azido and $R^4$ is hydrogen are prepared by reacting an alkyl 3-dioxolanyl-2,2-difluoro-3-hydroxypropionate prepared as described above with a trifluoromethanesulfonyl halide or other trifluoromethanesulfonyl compound having a good leaving group to provide the corresponding trifluoromethanesulfonyloxy substituted derivative which is converted to the azide. The azido derivative may be either cyclized to the lactone, which derivative may then be catalytically hydrogenated to the amine, or converted to the amine which is cyclized to the lactone. This reaction is represented by the following scheme:

The conditions under which the foregoing propionate is prepared are the same as those hereinbefore provided. The lactone is prepared by hydrolyses of the propionate derivative. Proper control of the hydrolysis step will cleave the ketonide function and will also cleave the ester group, providing the lactone in a single step. The hydrolysis reagent is preferably an acidic ion exchange resin, of which Dowex 50W-X12 (Dow Chemical Company) is most highly preferred. It is possible to carry out the process with other mild hydrolytic reagents, although it is possible that larger amounts of by-products may be obtained. For example, aqueous acetic acid, or other relatively strong acids such as propionic acid, formic acid, chloroacetic acid, oxalic acid and the like, may be used for the hydrolysis.

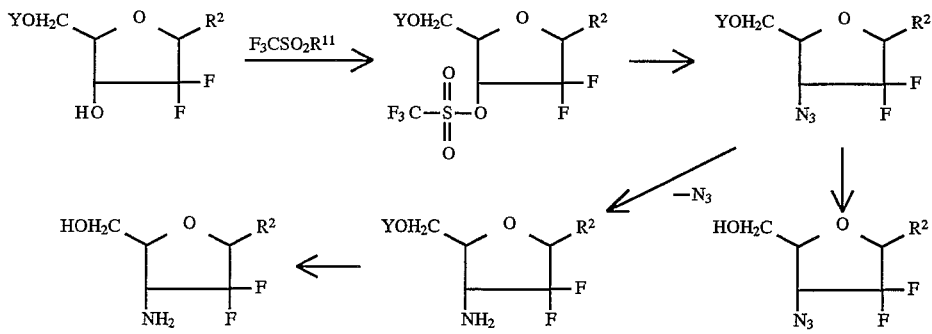

wherein $R^{11}$ is a good leaving group such as halogen, $R^{12}$ and $R^{13}$ are independently $C_1$–$C_3$ alkyl, and $R^{14}$ is $C_1$–$C_4$ alkyl.

The hydroxy groups of the lactone should be protected before its keto oxygen is reduced. The usual reaction conditions are used, depending on the nature of the protecting groups which may be chosen. For example, the t-butyldimethylsilyl group is most conveniently provided in the form of its trifluoromethanesulfonate, and the protection reaction is carried out in the presence of a base such as lutidine, pyridine and the like. Acyl protecting groups such as acetyl, benzoyl and the like are provided by reacting the lactone with an acylating agent such as an acyl chloride, bromide, cyanide or azide, or with an appropriate anhydride. The reactions are conveniently carried out in a basic solvent such as pyridine, quinoline or isoquinoline, or in a tertiary amine solvent such as triethylamine, tributylamine, methylpiperidine and the like. The reaction may also be carried out in an inert solvent, to which an acid scavenger, such as a tertiary amine, has been added. Acylation catalysts such as 4-dimethylaminopyridine or 4-pyrrolidinopyridine may be used in the reaction, if desired. The acylation reactions which provide protecting groups on the hydroxy groups are carried out at moderate temperatures in the range of from −25° C. to 100° C. Such acylations may also be performed by acid-catalyzed reactions of the appropriate carboxylic acids, in inert organic solvents or neat. Acid catalysts such as sulfuric acid, polyphosphoric acid, methanesulfonic acid and the like are used.

Acyl protecting groups may also be provided by forming an active ester of the appropriate acid, such as the esters formed by such known reagents as dicyclohexylcarbodimide, acylimidazoles, nitrophenols, pentachlorophenol, N-hydroxysuccinimide and 1-hydroxybenzotriazole.

Protecting groups of the ether type are placed by reacting the lactone with, for example, an appropriate diazo compound, such as diazomethane, phenyldiazomethane or a silyldiazomethane. Such reactions are commonly and effectively carried out in solvents including esters such as ethyl acetate, halogenated solvents including dichloromethane and chloroform, and ethers including diethyl ether and tetrahydrofuran. The process is usually carried out at low temperatures from about −50° C. to about 0° C. Such ether-forming reactions may also be carried out with the assistance of reagents such as trimethyloxosulfonium hydroxide, trimethylsulfonium hydroxide and trimethylselenonium hydroxide, in solvents such as dimethylsulfoxide, dimethylformamide, hexamethylphosphoramide, acetone, acetonitrile and the like.

The silyl protecting groups discussed above are placed on the hydroxy groups by the conventional methods, such as by reaction with the appropriate silylcarboxamide or bis (substituted-silyl)carboxamide, or an appropriately substituted silazane. Suitably substituted silyl methanesulfonates, toluenesulfonates and the like are also useful. An equivalent of a base is usually necessary in the reaction mixture, unless a basic solvent such as is discussed above is used as the reaction medium.

When the hydroxy groups have been protected, the keto oxygen of the lactone is reduced to the alcohol, forming the protected 2,3-deoxy-2,2-difluororibose or xylose of this invention. The most preferred reducing agent is lithium tri-t-butoxy aluminum hydride, used at a low temperature in the range of about −100° C. to −20° C. It is necessary to carry out the reduction very carefully, in order to avoid reducing conditions so vigorous that the ring is opened at the oxygen atom. Other reducing agents such as lithium aluminum hydride; alkylaluminum compounds such as diisobutylaluminum hydride and lithium t-butylalumino hydride; alkoxyaluminum hydrides such as lithium trimethoxyaluminum hydride; sodium alkoxborohydrides such as sodium hydridotri-sec-butoxyborate; organoborane reagents such as K-selectride and lithium triethylborohydride and chiral organoboranes such as Alpine–H, can also be used for the reduction, but it is necessary to keep the temperature quite low, at about −20° C. to about −100° C., and to assure that the hydride is destroyed before the temperature is allowed to rise toward ambient. Accordingly, a solvent with a very low freezing point must be used in the reduction step. Toluene is convenient; other solvents can of course be used, including lower alkanols, especially ethanol, ethers such as diethyl ether, tetrahydrofuran and the like.

The nucleoside compounds of the present invention as defined by Formula I may also be prepared by first preparing the appropriately substituted carbohydrate moiety and then attaching the carbohydrate to the desired base according to standard procedures. An appropriate leaving group must be placed at the 1-position of the carbohydrate, in order to obtain efficient reaction with the base. The preferred leaving group is methanesulfonyl, which is readily provided by reaction with methanesulfonyl chloride in the presence of an equivalent amount of a suitable acid scavenger such as triethylamine and the like. Other sulfonyl leaving groups, particularly toluenesulfonyl, are provided in the same way by reaction with the appropriate sulfonyl halide.

When a chloro or bromo leaving group is to be used, it is frequently convenient to first make the 1-acetate derivative, for instance by reaction with acetic anhydride, or another source of acetyl groups, in he presence of an equivalent or more of an acid scavenger. Then the acetate group is displaced with gaseous hydrogen bromide or hydrogen chloride, at a low temperature such as about −50° C. to about 0° C. Since the gaseous hydrogen halide may tend to remove the protecting groups, especially silyl protecting groups, it is necessary to operate this step at quite a low temperature and to add the hydrogen halide slowly in small increments.

The bases used to form the compounds of the present invention are commonly known to organic chemists, and no discussion of their synthesis is necessary. However, the primary amino groups which are present on some of the bases should be protected before the base is coupled with the carbohydrate. The usual amino-protecting groups are used, including silyl groups such as have been discussed, as well as such typical groups as t-butoxycarbonyl, benzyloxycarbonyl, 4-methoxybenzyloxycarbonyl, 4-nitrobenzyloxycarbonyl, formyl, acetyl, and the like.

It is often advisable to convert keto oxygen atoms on the bases to the enol form, in order to make the bases more highly aromatic and thereby allow more ready attack of the base by the carbohydrate. It is most convenient to enolize the oxygens by providing silyl protecting groups for them. The usual silyl protecting groups as discussed above are used for this purpose, also.

The reaction between the protected carbohydrate and the base is preferably carried out neat at an elevated temperature in the range of from about 50° C. to about 200° C. It is possible, however, to use relatively high-boiling solvents for the reaction, such as dimethylformamide, dimethylacetamide, hexamethylphosphoramide and the like. However, if the coupling reaction is carried out under elevated pressure, to avoid distillation of a low-boiling solvent, any convenient inert reaction solvent can be used.

The coupling reaction may be done at low temperatures if a reaction initiator, such as a trifluoromethanesulfonyloxysilane, is used. The usual inert reaction solvents, as discussed above, may be used at temperatures in the range of from about ambient to about 100° C.

The final step of the reaction sequence is the removal of the protecting groups. Most silyl protecting groups are easily cleaved by contact with water or an alcohol. The t-butyldimethylsilyl protecting group requires acid conditions, such as contact with gaseous hydrogen halide or aqueous trifluoroacetic acid for its removal.

Acyl protecting groups are removed by simple hydrolysis with strong or moderately strong bases, such as alkali metal hydroxides, at temperatures from about the ambient temperature to about 100°. At least one equivalent of base is needed for each protecting group, of course. Such hydrolyses are conveniently carried out in hydroxylic solvents, especially aqueous alkanols. The reactions may be also carried out, however, in any convenient solvent, such as polyols including ethylene glycol, ethers such as tetrahydrofuran and the like, ketones such as acetone and methyl ethyl ketone and other polar solvents such as dimethylsulfoxide. The cleavage of acyl protecting groups may also be performed with other bases, including, for example, sodium methoxide, potassium t-butoxide, hydrazine, hydroxylamine, ammonia, alkali metal amides and secondary amines such as diethylamine and the like. The acyl protecting groups can also be removed with acid catalysts, such as methanesulfonic acid, hydrochloric acid, hydrobromic acid, sulfuric acid, or with acidic ion exchange resins. It is preferred to carry out such hydrolyses at a relatively high temperature, such as the reflux temperature of the mixture, but temperatures as low as ambient may be used when particularly strong acids are used.

The removal of protecting groups which are ethers is carried out by known methods, for example, with ethanethiol and aluminum chloride.

None of the reaction steps require unusual excesses of the reactants. As usual in organic syntheses, it is advisable and economical to use a moderate excess, in the range of 1.05× to 2×, for example, of the cheaper reagents to assure that the costlier ones are consumed.

As has been noted above, the β-nucleosides of this invention are preferred. A particularly convenient enzymatic process has been discovered for isolating the β-nucleosides wherein $R^2$ is 2-amino-6-oxo-9H-purine. The process is carried out by reacting the racemic mixture of α- and β-nucleosides wherein $R^2$ is 2,6-diamino-9H-purine with adenosine deaminase, preferably Type I adenosine deaminase. The enzyme preferentially deaminates the 6-position of the β-nucleoside.

In the above isolation process, a catalytic to approximately an equimolar or excess amount of adenosine deaminase is added to a solution of the appropriate starting material in a suitable solvent. While a variety of solvents may be used, preferred solvents include the polar solvents such as the alcohols or water, which is preferred. The reaction is substantially complete after about 10 minutes to about 12 hours when conducted at a temperature in the range of about 0° C. to about 100° C. The reaction is preferably conducted for approximately 1 to 4 hours at a temperature in the range of about 20° C. to about 25° C.

If the foregoing reaction is allowed to proceed beyond the approximate maximum time indicated, the quantity of α-isomer produced will increase accordingly. Therefore, to maximize the amount of β-isomer synthesized it is preferred to follow the progress of the reaction by high performance liquid chromatography or thin layer chromatography.

The desired β-difluoronucleoside prepared by either process is readily recovered by standard techniques, such as extracting the desired compound into an organic solvent or, preferably, collecting the precipitated solid by vacuum filtration. The desired compound may be further purified if desired by crystallization from common solvents or column chromatography over solid supports such as silica gel or alumina, and especially $C_{18}$ high performance liquid chromatography. However, such additional purification is not usually needed.

The pharmaceutically acceptable acid addition salts of the invention are typically formed by reacting a 2',3'-dideoxy-2',2'-difluoronucleoside of the invention with an equimolar or excess amount of acid. The reactants are generally combined in a mutual solvent such as diethyl ether or benzene, and the salt normally precipitates out of solution within about one hour to 10 days, and can be isolated by filtration.

The compounds employed as starting materials in the synthesis of the compounds of the invention are well known and readily synthesized by standard procedures commonly employed by those of ordinary skill in the art. The 1-substituted-2-deoxy-2,2-difluororibose and -xylose derivatives are taught in U.S. Pat. Nos. 4,526,988 and 4,692,434, herein incorporated by reference.

The following Examples further illustrate specific compounds of the present invention. The Examples are not intended to be limiting to the scope of the invention in any respect and should not be so construed.

Example 1

β-1'-(4-Amino-2-oxo-1H-pyrimidin-1-yl)-2',3'-dideoxy-2',2'-difluororibose

A. β-1'-[4-(2,2-dimethyl-1-oxopropylamino)-2-oxo-1H-pyrimidin-1-yl]-5'-(2,2-dimethyl-1-oxopropyloxy)-2'-deoxy-2,2',2'-difluororibose A mixture of 0.9 g (0.003 mol) of β-1'-(4-amino-2-oxy-1H-pyrimidin-1-yl)-2'-deoxy-2',2'-difluororibose and 0.726 g (0.742 ml, 0.006 mol) of pivaloyl chloride in 10 ml of dry pyridine was refluxed for approximately 3½ hours with stirring. The pyridine was removed under vacuum at 45° C. The resulting suspension was dissolved in toluene and concentrated again under vacuum. The residue was dissolved in ethyl acetate and the resulting solution was washed once with water, once with 2N hydrochloric acid, once with a saturated sodium bicarbonate solution, once with water and finally once with a saturated sodium chloride solution. The organic phase was dried over anhydrous sodium sulfate and concentrated under vacuum to provide a white residue. The residue was dissolved in 150 ml of boiling ethyl acetate which was then concentrated to crystallization. The crystals were filtered and dried under vacuum at 50° C. to provide 0,656 g of β-1'-[4-(2,2-dimethyl-1-oxopropylamino)-2'-oxo-1H-pyrimidin-1-yl]-5'-(2,2-dimethyl-1-oxopropyloxy)-2'-deoxy-2',2'-difluororibose.

B. β-1'-[4-(2,2-dimethyl-1-oxopropylamino)-2-oxy-1H-pyrimidin-1-yl]-5'-(2,2-dimethyl-1-oxopropyloxy)-3'-(O-phenylcarbonothiooxy)-2'-deoxy-2',2'-difluororibose To a solution of 0.65 g (1.51 mmol) of β-1'-[4-(2,2-dimethyl-1-oxopropylamino)-2-oxo-1H-pyrimidin-1-yl]-5'-(2,2-dimethyl-1-oxopropyloxy)-2'-deoxy-2',2'-difluororibose and 0.02 g of 4-dimethylaminopyridine (DMAP) in 13 ml of dry pyridine under a nitrogen atmosphere was added 0.286 g (0.23 ml, 1.66 mmol) of phenyl chlorothionocarbonate. The reaction mixture was stirred at room temperature overnight. A thin layer chromatograph in methylene chloride:methanol (19:1, v:v) indicated that no starting material was present. The reaction mixture was concentrated under vacuum at 50° C. The residue was combined with toluene and the resulting mixture was again concentrated under vacuum. The residue was dissolved in ethyl acetate and water and washed once with 2N hydrochloric acid, once with a saturated sodium bicarbonate solution, once with water and once with saturated sodium chloride solution. The organic phase was dried over anhydrous sodium sulfate and concentrated under vacuum to provide 0.87 g of β-1'-[4-(2,2-dimethyl-1-oxopropylamino) -2-oxo-1H-pyrimidin-1-yl]-5'-(2,2-dimethyl-1-oxopropyloxy)-3'-(O-phenylcarbonothiooxy)-2'-deoxy-2', 2'-difluororibose as a yellow orange solid.

C. β-1'-[4-(2,2-dimethyl-1-oxopropylamino)-2-oxy-1H-pyrimidin-1-yl]-5'-(2,2-dimethyl-1-oxopropyloxy)-2',3'-dideoxy-2',2'-difluororibose.

To a solution of 0.87 g (1.5 mmol) of β-1'-[4-(2,2-dimethyl-1-oxopropylamino)-2-oxo-1H-pyrimidin-1-yl]-5'-(2,2-dimethyl-1-oxopropyloxy)-3'-(O-phenylcarbonothiooxy)- 2-deoxy-2,2-difluororibose and 0.03 g of 2,2'-azobis[2-methylpropionitrile] (AIBN) in 19 ml of dry toluene under a nitrogen atmosphere was added 0.81 ml (3.1 mmol) of 3.79M tributyltin hydride. The reaction mixture was heated at 85° C. for 3½ hours and an additional 0.12 ml of tributyltin hydride was added to the reaction mixture. The reaction mixture was stirred at 85° C. for one hour and concentrated under vacuum at about 50° C. The residue was triturated twice with 15 ml of hexane. The hexane was decanted and the residue was concentrated under vacuum to provide a residue which was chromatographed over silicon dioxide employing methylene chloride:methanol (49:1, v:v). Fractions containing the major component were combined and the solvent was evaporated therefrom to provide 0.38 g of β-1'-[4-(2,2-dimethyl-1-oxopropylamino)-2-oxo-1H-pyrimidin-1-yl]-5'-(2,2-dimethyl-1-oxopropyloxy)-2',3'-dideoxy-2',2'-difluororibose.

D. To a solution of 0.37 g (0.89 mmol) of β-1'-[4-(2,2-dimethyl-1-oxopropylamino)-2-oxo-1H-pyrimidin-1-yl]-5'-(2,2-dimethyl-1-oxopropyloxy)-2',3'-dideoxy-2',2'-difluororibose in 20 ml of methanol was added 4 ml of concentrated ammonium hydroxide. The reaction mixture was sealed in a glass vial. The mixture was heated at 50° C. for 2 hours and then stirred at room temperature overnight. An additional 3 ml of ammonium hydroxide was added to the mixture. The mixture was heated at 60° C. for 3 hours. The mixture was heated for 10 minutes at 100° C., cooled and concentrated under vacuum. The residue was dissolved in ethyl acetate and water. The layers were separated. The aqueous layer was concentrated under vacuum to provide an oil which was dissolved in acetone. The resulting solution was concentrated under vacuum to provide 0.16 g of the desired compound β-1-(4-amino-2-oxo-1H-pyrimidin-1-yl) -2,3-dideoxy-2,2-difluororibose as a white foam. The foam was chromatographed on a Whatman Partisil 10 ODS-3 column, 250×10 mm, with 9:1 water:methanol to yield 0.11 g of purified product.

$^1$H-NMR (300 MHz, CD$_3$OD): δ2.50 (m, 2H, 3'-H);3.72 (d, 1H, 5B'-H); 3.90 (d, 1H, 5A'-H); 4.32 (m, 1H, 4'-H); 5.93 (d, 1H, 5-H); 6.25 (d, 1H, 1'-H); 8.02 (d, 1H, 6-H).

High resolution MS: obs 248.0847, calculated for M+1: C$_9$H$_{12}$N$_3$O$_3$F$_2$, 248.0847.

Example 2

β-1'-(2,6-diamino-9H-purin-9-yl)-2',3'-dideoxy-2,2-difluororibose

To a solution of 0.2 g (0.5 mmol) of β-1'-(2,6-diamino-9H-purin-9-yl)-5'-benzoyl-2'-deoxy-2',2'-difluororibose and 6 mg (0.05 mmol) of 4-dimethylaminopyridine in 5 ml of dry pyridine under a nitrogen atmosphere Was added 0.38 g (0.3 ml, 2.2 mmol) of phenyl chlorothionocarbonate. The reaction mixture was stirred at room temperature overnight. A thin layer chromatograph in methylene chloride:methanol (19:1, v/v) indicated that no starting material was present. The reaction mixture was evaporated to dryness and the residue was combined with toluene and the resulting mixture was again concentrated under vacuum. The residue was dissolved in ethyl acetate and washed once with water, once with 1.0N hydrochloric acid, once with a 10% by volume sodium bicarbonate solution, once with water and once with saturated sodium chloride solution. The organic phase was dried over anhydrous sodium sulfate and concentrated under vacuum to provide 0.25 g of β-1'-(2,6-diamino-9H-purin-9-yl)-5'-benzoyl-3'-(O-phenylcarbonothiooxy)-2'-deoxy-2',2'-difluororibose which was used without further workup. Mass spec. m/e=542=P.

To a solution of 0.25 g (.0.046 mmol) of the above intermediate and 10 mg of 2,2'-azobis[2-methylpropionitrile] in 10 ml of dry toluene under a nitrogen atmosphere was added 0.24 ml (0.92 mmol) of tributyltin hydride. The reaction mixture was heated at 85° C. for 12 hours and an additional 0.06 ml (0.23 mmol) of tributyltin hydride was added to the reaction mixture. The reaction mixture was stirred at 85° C. for 8 hours and concentrated under vacuum at about 50° C. The residue was taken up in acetonitrile and washed with hexane. The acetonitrile layer was concentrated under vacuum to provide an oil. The oil was chromatographed over silicon dioxide employing methylene chloride:methanol (19:1, v:v). Fractions containing the major component were combined and the solvent was evaporated therefrom to provide 20 mg of β-1'-(2,6-diamino-9H-purin-9-yl)-5'-benzoyl-2',3'-dideoxy-2',2'-difluororibose. Mass spec. m/e=390=P.

A solution of 20 mg (0.05 mmol) of the above intermediate in methanol (10 ml) was saturated with ammonia at 0° C. The solution was then warmed to ambient temperature and stirred overnight. Solvent was evaporated and the residue was chromatographed on silica gel, eluting with a gradient from 5% methanol in methylene chloride to 10% methanol in methylene chloride. The product fractions were combined and evaporated to yield 6.3 mg of β-1'-(2,6-diamino-9H-purin-9-yl)-2',3'-dideoxy-2',2'-difluororibose. $^1$H-NMR (CD$_3$OD, 300 MHz) δ2.55 (m, 1H, 3'A); 2.85 (m, 1H, 3'B); 3.7 (m, 1H, 5'A); 3.9 (m, 1H, 5'B); 4.38 (m, 1H, 4'); 6.1 (m, 1H, 1'); 8.05 (s, 1H, H-8). Mass spec. m/e=286= P.

Example 3

β-1'-(2-amino-6-oxo-9H-purin-9-yl)-2',3'-dideoxy-2',2'-difluororibose

To a solution of 12 mg (0.042 mmol) of the compound of Example 2 in water (2 ml) at ambient temperature was added adenosine deaminase (Sigma). The reaction was followed by liquid chromatography (C$_{18}$, 15% methanol in water, 1 ml/min) and enzyme was added periodically until the reaction appeared to be complete. The reaction mixture was heated at reflux to deactivate the enzyme, and was then evaporated to a solid. The solid residue was recrystallized from D$_2$O to yield 6.3 mg of the desired product. $^1$H-NMR (D$_2$O, 300 MHz) δ2.67 (m, 2H, 3'); 3.75 (m, 1H, 5'A); 3.9 (m, 1H, 5'B); 4.5 (m, 1H, 4'); 6.1 (m, 1H, 1'); 8.0 (s, 1H, H-8). Mass spec. m/e=287=P.

Example 4

β-1'-(5-methyl-2,4-dioxo-1H,3H-pyrimidin-1-yl)-3'-azido-2',3'-dideoxy-2',2'-difluororibose A suspension of 4.0 g (14 mmol) of β-1'-(5-methyl-2,4-dioxo-1H,3H-pyrimidin-1-yl)-2'-deoxy-2',2'-difluororibose and 4.8 g (17 mmol) of triphenylmethyl chloride in 40 ml of dry pyridine were heated at reflux for 3 hours and then stirred overnight at ambient temperature. The reaction mixture was then poured into ice water and extracted three times with ether. The organic layer was washed with 1.0N hydrochloric acid and then with water and saturated aqueous sodium chloride, dried over sodium sulfate and evaporated under reduced pressure to yield 7.34 g of β-1'-(5-methyl-2,4-dioxo-1H,3H-pyrimidin-1-yl)-5'-triphenylmethyl-2'-deoxy-2',2'-difluororibose. Mass spec. m/e=520=P.

To a solution of 7.12 g (14 mmol) of the above intermediate in methylene chloride (248 ml) and pyridine (4.5 ml) was added 5.2 g (19 mmol) of triflic anhydride at 0° C. The reaction mixture was stirred at 0° C. for 3 hours then evaporated under reduced pressure. The resulting residue was mixed with ethyl acetate and washed with cold water, saturated sodium, bicarbonate, and saturated sodium chloride solution and evaporated to dryness. The residue was mixed with toluene and stripped to dryness to yield 9.13 g of β-1'-(5-methyl-2,4-dioxo-1H,3H-pyrimidin-1-yl)-5'-triphenylmethyl-3'-trifluoromethylsulfonyl-2'-deoxy-2',2'-difluororibose. $^1$H-NMR (CDCl$_3$, 300 MHz) δ2.05 (s, 3H, 5-CH$_3$); 3.45 (m, 1H, 5'A); 3.7 (m, 1H, 5'B); 4.28 (m, 1H, 4'); 5.5 (m, 1H, 3'); 6.3 (m, 1H, 1'); 7.35 (m, 16H, Ph$_3$ & H-6). Mass spec. m/e=652=P.

A solution of 9.13 g (14 mmol) of the above intermediate and 9.8 ml of 1.0N sodium hydroxide in ethanol (100 ml) was stirred at ambient temperature for 12 hours. The reaction mixture was neutralized with 1.0N hydrochloric acid and then the ethanol was evaporated resulting in a precipitate which was collected and dried to obtain 2.97 g of β-1'-(5-methyl-2,4-dioxo-1H,3H-pyrimidin-1-yl)-5'-triphenylmethyl-3'-(2-anhydro)-2'-deoxy-2',2'-difluororibose. $^1$H NMR (CDCl$_3$, 300 MHz) δ1.95 (s, 3H, 5-CH$_3$); 3.4 (m, 2H, 5'A&B); 4.5 (m, 1H, 4'); 4.85 (m, 1H, 3'); 5.3 (m, 1H, 1'); 6.9 (s, 1H, H-6); 7.3 (m, 15H, Ph$_3$). Mass spec. m/e=502=P.

A suspension of 2.7 g (5.4 mmol) of the above intermediate in 80% acetic acid (54 ml) was heated at reflux for 2.5 hours. The solution was allowed to cool and the precipitate that formed was collected and identified as triphenylmethanol. The filtrate was evaporated to dryness and then mixed with water and extracted with hexane. The aqueous layer was evaporated to dryness to yield 1.65 g of β-1'-(5-methyl-2,4-dioxo-1H,3H-pyrimidin-1-yl)-2'-deoxy-2',2'-difluoroxylose. $^1$H-NMR (CD$_3$OD, 300 MHz) δ1.95 (s, 3H, 5-CH$_3$); 4.3 (series of M, 4H, 3', 4'& 5' A&B); 6.15 (dd, 1H, 1'); 7.6 (s, 1H, H-6). Mass spec. m/e=278=P.

A solution of 0.25 g (0.9 mmol) of the above intermediate, glacial acetic acid (5 ml) and water (0.06 ml, 3.3 mmol) was heated at reflux for 8 hours. The reaction mixture was allowed to cool and then evaporated to dryness under reduced pressure. The resulting residue was chromatographed on a silica gel column eluting with 5% methanol in methylene chloride. The product fractions were collected, combined and evaporated to dryness to yield 0.2 g of β-1'-(5-methyl-2,4-dioxo-1H,3H-pyrimidin-1-yl)-5'-acetyl-2'-deoxy-2',2'-difluoroxylose.

To a solution of 0.1 g (0.3 mmol) of the above intermediate in pyridine (0.066 ml, 0.82 mmol) and methylene chloride (8 ml) at 0° C. was added 0.115 g (0.41 mmol) triflic anhydride. The reaction mixture was stirred at 0° C. for 1.5 hours at which time it was added to a mixture of ice and saturated sodium bicarbonate solution. The organic layer was separated, washed with saturated sodium chloride, dried over sodium sulfate and evaporated to dryness to yield 0.14 g of β-1'-(5-methyl-2,4-dioxo-1H,3H-pyrimidin-1-yl)-5'-acetyl- 3'-trifluoromethanesulfonyl-2'-deoxy-2',2'-difluoroxylose. $^1$H-NMR (CDCl$_3$, 300 MHz) δ1.95 (s, 3H, 5-CH$_3$); 2.05 (s, 3H, COCH$_3$); 4.45 (m, 3H, 4'& 5'A&B); 5.3 (m, 1H, 3'); 6.35 (m, 1H, 1'); 7.05 (s, 1H, 6-H). Mass spec. m/e=452=P.

A solution of 0.13 g (0.28 mmol) of the above intermediate and 0.14 g (2.8 mmol) of lithium azide in dimethylformamide (5 ml) was stirred for 12 hours at −30° C. The reaction was evaporated and the resulting residue was stripped twice with toluene. The residue was dissolved in ethyl acetate and washed with water, dried and evaporated under reduced pressure to yield 0.06 g of β-1'-(5-methyl-2,4-dioxo-1H,3H-pyrimidin-1-yl)-5'-acetyl-3'-azido-2',3'-dideoxy-2',2'-difluororibose. Mass spec. m/e=345=P. IR 2120 cm$^{-1}$.

A solution of 0.06 g (0.17 mmol) of the above intermediate in a saturated solution of anhydrous ammonia in methanol (20 ml) was stirred at −8° C. for 2 hours. The solution was evaporated to dryness under vacuum at 40° C. The residue was chromatographed on silica gel eluting with 7% methanol in methylene chloride containing 1% v/v concentrated ammonium hydroxide. The main fraction was collected, combined and evaporated to dryness. The material was further purified by preparative HPLC using a C18 reverse phase column eluting with water/methanol, 1/1. The second compound to elute from the column was identified as the desired product, (12.1 mg). $^1$H-NMR (CD$_3$OD, 300 MHz) δ1.75 (s, 3H, 5-CH$_3$); 3.7 (m, 1H, 5'A); 3.9 (m, 2H, 3'&5'B); 4.5 (m, 1H, 4'); 6.2 (apparent t, 1H, 1'); 7.7 (s, 1H, H-6). High resolution mass spec. obs. 304.08575, calculated for M+1:C$_{10}$H$_{12}$N$_5$O$_4$F$_2$, 304.08575. I.R. 2120 cm$^{-1}$.

Example 5

β-1'-(5-methyl-2,4-dioxo-1H,3H-pyrimidin-1-yl)-2', 3'-dideoxy-2',2'-difluororibose To a solution of 0.2 g (0.63 mmol) of β-1'-(5-methyl-2, 4-dioxo-1H,3-pyrimidin-1-yl)-5'-acetyl-2'-deoxy-2',2'-difluororibose and 0.02 g of 4-dimethylaminopyridine in 5 ml of dry pyridine under a nitrogen atmosphere was added 0.13 g (0.10 ml, 0.75 mmol) of phenyl chlorothionocarbonate. The reaction mixture was stirred at room temperature overnight. A thin layer chromatograph in methylene chloride:methanol (19:1, v/v) indicated that no starting material was present. The reaction mixture was stripped three times with toluene. The residue was dissolved in ethyl acetate and water and washed once with 1.0N hydrochloric acid, once with 10% by volume sodium bicarbonate solution, once with water and once with saturated sodium chloride solution. The organic phase was dried over anhydrous sodium sulfate and concentrated under vacuum to provide 0.47 g of β-1'-(5-methyl-2,4-dioxo-1H,3H-pyrimidin-1-yl)-5'-acetyl-3'-(O-phenylcarbonothiooxy)-2'-deoxy-2',2'-difluororibose which was used without further workup.

To a solution of 0.47 g (0.63 mmol) of the above intermediate and 0.02 g of 2,2'-azobis[2-methylpropionitrile] in 9 ml of dry toluene under a nitrogen atmosphere was added 0.34 ml (1.3 mmol) of tributyltin hydride. The reaction mixture was heated at 85° C. for 3.5 hours and an additional 0.17 ml of tributyltin hydride was added to the reaction mixture. The reaction mixture was stirred at 85° C. for one hour and concentrated under vacuum at about 50° C. The residue was triturated twice with 15 ml of hexane. The hexane was decanted and the residue was concentrated under vacuum. The residue was chromatographed over silicon dioxide employing ethyl acetate/hexane (1.5/1, v/v). Fractions containing the major component were combined and the solvent was evaporated therefrom to provide 0.09 g of β-1'-(5-methyl-2,4-dioxo-1H,3H-pyrimidin-1-yl)-5'-acetyl-2',3'-dideoxy-2',2'-difluororibose.

A solution of 0.09 (0.30 mmol) of the above intermediate was stirred in a saturated solution of anhydrous ammonia in methanol (10 ml) at 0°–5° C. for 2 hours. The solution was evaporated to dryness under vacuum. The white residue was dissolved in a minimum amount of methanol and 20 ml of methylene chloride was added. This solution was stripped to 3 ml volume and more methylene chloride was added until crystals formed. The crystals were collected to yield 51 mg of the desired product. $^1$H-NMR (CD$_3$OD, 300 MHz) δ1.85 (s, 3H, 5-CH$_3$); 2.5 (m, 2H, 2'); 3.65 (m, 1H, 5'A); 3.9 (m, 1H, 5'B); 4.3 (m, 1H, 4'); 6.1 (m, 1H, 1'); 7.8 (s, 1H, 6-H). Mass spec. m/e=262=P.

Preparation 1

β1'-(2,6-diamino-9H-purin-9-yl)-5'-benzoyl-2'-deoxy-2',2'-difluororibose

To a solution of 11.16 g (22 mmol) of α& β-1'-(2,6-diamino-9H-purin-9-yl)-3',5'-dibenzoyl-2'-deoxy-2',2'-difluororibose was added hydrazine (0.7 g, 22 mmol). The solution was heated at 65° C. for three hours. An additional amount of hydrazine was added (0.35 g, 11 mmol) and heating was continued for four hours. One additional amount of hydrazine (0.35 g, 11 mmol) was added and the solution was heated for four more hours. The reaction mixture was allowed to cool and the solvent was removed under reduced pressure. The resulting residue was put onto a silica gel column and eluted with a gradient from 2.5% methanol in methylene chloride to 5% methanol in methylene chloride. The remaining amount of starting material came off the column first followed by the alpha anomer (4.96 g) and then the beta anomer (1.75 g). $^1$H-NMR (DMSO d$_6$, 300 MHz) δ4.25 (m, 1H, 3'); 4.7 (m, 3H, 5' A&B, 4'); 5.95 (bs, 2H, NH$_2$); 6.15 (m, 1H, 1'); 6.5 (d, 1H, OH); 6.85 (bs, 2H, NH$_2$); 7.7 (m, 5H, Bz); 7.82 (s, 1H, C-8). Mass spec. =407=P+1.

Example 6

α and β-1'-(6-amino-9H-purin-9-yl)-2',3'-di-deoxy-2', 2'-difluororibose

To a solution of 22.1 g (58 mmol) of 3,5-bis(benzoyl)-2-deoxy-2,2-difluororibose and 8.0 g (116 mmol) of imidazole in 410 ml of dimethylformamide (DMF) was added 8.8 g (58 mmol) of t-butyldimethylsilyl chloride. This reaction mixture was stirred for 12 hours at ambient temperature. The mixture was evaporated to dryness under reduced pressure. The residue was mixed with ethyl acetate and washed with 1.0N hydrochloric acid, saturated sodium bicarbonate, water, saturated sodium chloride solution, dried with sodium sulfate and evaporated to dryness under reduced pressure to yield 24.5 g of 1-(t-butyldimethylsilyloxy)-3, 5-bis(benzoyl)-2-deoxy-2,2-difluororibose.

To a solution of 19.12 g (39 mmol) of the above intermediate dissolved in methanol (560 ml) and cooled to −20° C. was added solid sodium methoxide (1.79 g, 33 mmol) portionwise while maintaining the reaction temperature at −20° C. The reaction mixture was stirred at −20° C. for 3 hours at which time it was neutralized with acetic acid (2 g). The mixture was evaporated to a residue under reduced pressure at 40° C. The residue was mixed with water and ethyl acetate. The organic layer was separated and washed with water and saturated sodium chloride solution, dried with sodium sulfate and evaporated under reduced pressure. The resulting residue was chromatographed on silica gel and eluted with 4:1 hexane:ethyl acetate. The product fractions were combined and evaporated under reduced pressure to product fractions were combined and evaporated under reduced pressure to yield 10.4 g of 1-(t-butyldimethylsilyloxy)-5-benzoyl-2-deoxy-2,2-difluororibose. Mass spec. m/e=389=P+1, m/e=331=P-t-butyl.

To a solution of 10.4 g (27 mmol) of the above intermediate and 0.05 g of 4-dimethylaminopyridine in 220 ml of dry pyridine under a nitrogen atmosphere was added 4.6 g (3.7 ml, 27 mmol) of phenyl chlorothionocarbonate. The reaction mixture was stirred at room temperature overnight. The reaction mixture was concentrated under vacuum at 50° C. to provide 14.2 g of 1-(t-butyldimethylsilyloxy)-3-(O-phenylcarbonothiooxy)-5-benzoyl-2-deoxy-2,2-difluororibose which was used without further workup. Mass spec. m/e=467=P-t-butyl.

To a solution of 14.24 g (27 mmol) of the above intermediate and 0.05 g of 2,2'-azobis[2-methylpropionitrile]in 280 ml of dry toluene under a nitrogen atmosphere was added 14.32 ml (54 mmol) of tributyltin hydride. The reaction mixture was heated at 85° C. for 4.5 hours. The reaction mixture was evaporated therefrom to provide 30.57 g of crude 1-(t-butyldimethylsilyloxy)-5-benzoyl-2,3-di-deoxy-2,2-difluororibose which was used without further purification. $^1$H-NMR (CDCl$_3$, 300 MHz) δ0.15 (m, 6H, SiCH$_3$); 0.95 (m, 9H, t-butyl); 2.45 (m, 2H, 3'A&B); 4.5 (series of m, 3H, 4'&5'A&B); 5.2 (m, 1H, 1'); 7.8 (series of m, 5H, Bz).

To a solution of 1.0 g (2.7 mmol) of the above intermediate in 15 ml of tetrahydrofuran was added 5.4 ml (5.4 mmol) of a 1.0N solution of tetrabutyl ammonium fluoride in tetrahydrofuran. The reaction mixture was stirred at ambient temperature for 2 hours. The reaction mixture was evaporated under reduced pressure and the resulting residue was dissolved in ethyl acetate and washed with water, dried over sodium sulfate and evaporated under reduced pressure. The resulting oil was put on a silica gel column and eluted with a gradient from 5% ethyl acetate in hexane to 25% ethyl acetate in hexane. The product fractions were combined and evaporated under reduced pressure to yield 0.15 g of 5-benzoyl-2,3-dideoxy-2,2-difluororibose. Mass spec. m/e=258=P.

To a solution of 0.23 g (1.5 mmol) of 6-chloropurine in 10 ml of tetrahydrofuran was added 0.40 g (1.5 mmol) of triphenylphosphine and 0.26 g (1.5 mmol) of diethyl azodicarboxylate. To this solution was added a solution of 0.26 g (1.0 mmol) of the above intermediate in tetrahydrofuran. The reaction mixture was stirred at room temperature for approximately 12 hours. The solvent was evaporated under vacuum and the residue was chromatographed over silica and eluted with 2:1 hexane:ethyl acetate. Fractions containing the products were combined and the solvent was evaporated to provide 50 mg of α and β-1'-(6-chloro-9H-purin-9-yl)-5'-benzoyl-2',3'-dideoxy-2',2'-difluororibose. Mass spec. m/e=395=P+1.

A solution of 50 mg (0.127 mmol) of the above mixture of intermediates dissolved in 9 ml of methanol was saturated with anhydrous ammonia at about 0° C. The reaction flask was sealed, and the mixture was allowed to warm to room temperature. The mixture was stirred for about 12 hours at room temperature and the volatiles were evaporated under reduced pressure to provide 40 mg of the desired products as a mixture. Mass spec. m/e=271=P.

Example 7

1-t-butyldimethylsilyloxy-5-benzoyl-2-deoxy-2,2-difluororibose

To a solution of 0.97 g (2.0 mmol) of 1-(t-butyldimethylsilyloxy)-3,5-bis(benzoyl)-2-deoxy-2,2-difluororibose in tetrahydrofuran (40 ml) cooled to −78° C. were added 4.0 ml of a 1M solution of potassium t-butoxide in tetrahydrofuran (4.0 mmol) dropwise. The reaction mixture was stirred 15 minutes at −78° C. and was then quenched with 0.45 ml glacial acetic acid (8.0 mmol). The reaction mixture was diluted with ethyl acetate (100 ml) and washed with brine (50 ml). The separated organic layer was dried with sodium sulfate and evaporated under reduced pressure. The resulting residue was chromatographed on silica gel and eluted with hexane containing 10–15% ethyl acetate. The product fractions were combined and concentrated under reduced pressure to yield 0.724 g (93%) of 1-(t-butyldimethylsilyloxy)- 5-benzoyl-2-deoxy-2,2-difluororibose. Mass spec.: m/e=389=P+1, m/e=331=P-t-butyl.

IR (CHCl$_3$) 1722, 1276, 1115 cm$^1$; $^1$H NMR (300 MHz, CDCl$_3$) δ8.00–8.10 (m,2H, aromatics), 7.55–7.60 (m,1H, aromatic), 7.40–7.50 (m, 2H, aromatics), 5.28 (d,J=5.3 Hz,0.2H,1-H of minor isomer), 5.17 (d,J=7.1 Hz,0.8H,1-H of major isomer), 4.35–4.65 (m,3H,4-H and 5-CH$_2$), 4.05–4.18 (m, 1H,3-H), 2.50 (d,J=10 Hz,0.2H,OH of minor isomer), 2.39 (d,J=10 Hz,0.8H,OH of major isomer), 0.97 (s, 1.8H, t-butyl of minor isomer), 0.94 (s,7.2H, t-butyl of major isomer), 0.10–0.20 (m,6H, CH$_3$—Si).

Anal. Calcd for C$_{18}$H$_{26}$F$_2$O$_5$Si: C, 55.65; H, 6.75. Found: C, 55.42, H, 6.89.

Example 8

α-1'-(2,6-diamino-9H-purin-9-yl)-5'-benzoyl-2'-deoxy-2',2'-difluororibose

To a solution of 51 mg (0.1 mmol) of 1'-(2 6-diamino-9H-purin-9-yl)-3',5'-bis(benzoyl)-2'-deoxy-2',2'-difluororibose in tetrahydrofuran (5 ml) cooled to −78° C. were added 0.2 ml of 1M solution of potassium t-butoxide in tetrahydrofuran (0.2 mmol) dropwise. After stirring 2 hours at −78° C., an additional 0.2 ml of 1M potassium sium t-butoxide in tetrahydrofuran (0.2 mmol) were added to the reaction mixture and stirring at −78° C. was continued for 30 minutes. The reaction mixture was quenched with 2 ml of glacial acetic acid and was then allowed to warm to room temperature. The reaction mixture was then diluted with water (5 ml) and extracted well with ethyl acetate. Pooled organic extracts were washed with saturated aqueous sodium bicarbonate, dried with sodium sulfate and concentrated under reduced pressure. The resulting residue was chromatographed on silica gel and eluted with dichloromethane containing 5% methanol. The product fractions were concentrated under reduced pressure to yield 16.4 mg of α-1'-(2,6-diamino-9H-purin-9-yl)-5'-benzoyl-2'-deoxy-2',2'-difluororibose. A 4.9 mg portion of the β anomer was isolated from separate fractions.

Example 11

1-t-butyldimethylsilyloxy-5-benzoyl-3-trifluoromethane-sulfonyloxy-2-deoxy-2,2-difluoroxylose To a solution of 2.3 g (5.9 mmol) 1-t-butyldimethyl-silyloxy-5-benzoyl-2-deoxy-2,2-difluoroxylose in dichloromethane (100 ml) were added 7.2 ml (88.5 mmol) pyridine and the reaction mixture was cooled to −20° C. To this was then added a solution of 1.5 ml (8.9 mmol) trifluoromethanesulfonic anhydride in dichloromethane (20 mL) dropwise at such a rate as to maintain the temperature between −5° and −20° C. The reaction mixture was stirred for 40 minutes at −15° C. The reaction mixture was then allowed to warm to room temperature and was washed with saturated aqueous sodium bicarbonate. The remaining organic layer was dried over magnesium sulfate and concentrated under reduced pressure to give 2.8 g (90%) of the desired compound as a yellow oil. FD-MS: m/e=463(M−57, loss of t-butyl).

Example 12

1-t-butyldimethylsilyloxy-5-benzoyl-3-azido-2,3-dideoxy-2,2-difluororibose

To a solution of 4.53 g (8.7 mmol) 1-t-butyldimethylsilyloxy-5-benzoyl-3-trifluoromethanesulfonyloxy-2-deoxy-2,2-difluoroxylose in dimethylformamide (50 ml) were added 1.2 g (25.2 mmol) lithium azide and the reaction mixture was heated at 70° C. for 40 minutes. The reaction mixture was then concentrated under reduced pressure and the residue dissolved in ethyl acetate. This solution was washed several times with saturated aqueous sodium chloride, dried over sodium sulfate and concentrated under reduced pressure. The residue was redissolved in a small amount of ethyl acetate and poured over a pad of silica gel, eluting with ethyl acetate. The filtrates were concentrated under reduced pressure to give 2.09 g (58%) of the desired compound as a colorless oil. FD-MS: m/e=356, (M−57, loss of t-butyl), 357((M+1)-57, loss of t-butyl). IR(neat): 2114 cm$^{-1}$, N$_3$.

Example 13

α and β-5-benzoyl-3-azido-2,3-dideoxy-2,2-difluororibose

A solution of 1.0 g (2.4 mmol) α-1-t-butyldimethylsilyl-oxy-5-benzoyl-3-azido-2,3-dideoxy-2,2-difluororibose in 10 ml each of trifluoroacetic acid, water and tetrahydrofuran was heated at 65° C. for 3 hours. The volatiles were removed under reduced pressure to give the title compound as a brown oil in quantitative crude yield. The material was used without further purification. IR: 2115 cm$^{-1}$, N$_3$; 3400 cm$^{-1}$, OH. FD-MS: m/e=300(M+1).

Example 14

α and β-1-mesyloxy-5-benzoyl-3-azido-2,3-dideoxy-2,2-difluororibose

To a solution of 700 mg (2.34 mmol) α and β-5-benzoyl-3-azido-2,3-dideoxy-2,2-difluororibose in dichloromethane (10 ml) were added 0.4 ml (2.70 mmol) triethylamine and the reaction mixture was cooled to 5° C. To this were added 0.2 ml (2.58 mmol) methanesulfonyl chloride dropwise at such a rate that the temperature remained below 10° C. The reaction mixture was stirred for 2 hours at room temperature and was then quenched by the addition of cold 1N hydrochloric acid (6 ml). The organic layer was washed with water and the aqueous layers were reextracted with dichloromethane. The combined organic extracts were washed with saturated aqueous sodium chloride, dried over sodium sulfate and concentrated under reduced pressure to give the crude product as a brown oil. The product was purified by silica gel chromatography, eluting with hexane containing 0–25% ethyl acetate. 177 mg of pure β-anomer, 70 mg of pure α-anomer and 295 mg of a 2:1(α:β)mixture were recovered from different fractions of the chromatography to give a total yield of 542 mg (61%) of the title compounds. FAB-MS: m/e=378, 379(M+1, M+2), m/e=282(M-95, loss of methanesulfonyl). IR(neat): 2216 cm$^{-1}$, $N_3$.

Example 15

α and β-1'-(6-chloro-9H-purin-9-yl)-5'-benzoyl-2', 3'-dideoxy-3'-azido-2',2'-difluororibose To a solution of 144 mg (0.93 mmol) 6-chloropurine, 244 mg (0.93 mmol) triphenylphosphine and 162 mg (0.93 mmol) diethylazodicarboxylate in tetrahydrofuran (5 ml) were added a solution of 278 mg (0.93 mmol) α and β-5-benzoyl-3-azido-2-deoxy-2,2-difluororibose in tetrahydrofuran (10 ml) dropwise and the reaction mixture was stirred for 18 hours at room temperature. Volatiles were removed under reduced pressure and the resulting brown oil was triturated with diethyl ether. The resulting suspension was filtered and the filtrate concentrated under reduced pressure to give 836 mg of a crude brown oil. Purification was accomplished by $C_{18}$-reverse phase chromatography, eluting with 55% acetonitrile in water. Fractions containing product were combined and concentrated under reduced pressure to give 110.9 mg (27%) of the title compounds as a colorless oil (α:β1:1). The oil was dissolved in isopropanol and 25.3 mg of α-1'-(6-chloro-9H-Purin-9-yl)-5'-benzoyl-3'-azido-2',3,-dideoxy-2', 2'-difluororibose were recovered as a colorless, crystalline solid. $^1$H-NMR(300 MHz, $CDCl_3$): δ8.82(d, 1H, J=small), 8.38(d, 1H, J=small), 8.15 (d, 1H), 7.52(m, 4H), 6.63(t, 1H, J=9 Hz), 4.82(m, 1H), 4.70(m, 2H), 4.45(m, 1H).

Example 16

α-1'-(6-amino-9H-purin-9-yl)-3'-azido-2',3'-dideoxy-2',2'-difluororibose

A solution of 27 mg (0.062 mmol) α-1'-(6-chloro-9H-purin-9-yl)-5'-benzoyl-3'-azido-2',3'-dideoxy-2',2'-difluororibose in isopropanol (12 ml) was placed in a steel bomb and the solution cooled to 0° C. Gaseous ammonia was bubbled into the reaction mixture for 5 minutes. The bomb was sealed and the reaction mixture heated at 80° C. for two days. The reaction mixture was cooled to room temperature and concentrated under reduced pressure. The residue was purified by reverse phase chromatography on a $C_{18}$ column eluting with 15% acetonitrile in water at a flow rate of 9 ml/min. Fractions containing product were concentrated under reduced pressure to give 11.8 mg (61%) of the title compound as a colorless solid. FAB-MS: m/e=313 (M+1), 315(M+3). IR: 2116 cm$^{-1}$, $N_3$. $^1$H-NMR(300 MHz, $d_7$-DMF): δ8.41(d, 1H, J=2.4 Hz), 8.22(s, 1H), 7.47(s, br, 2H), 6.70(dd, 1H, J=11.5, 6.2 Hz), 5.01(m, 1H), 4.76(m, 1H), 3.85(m, 2H). $^{13}$C-NMR(300 MHz, $d_7$-DMF): 157.30 (C-6), 154.05(C-2), 150.49(C-4), 139.80(C-8), 123.65(C-2'), 119.43(C-5), 84.0(C-1'), 82.74(C-4'), 61.97(C-3'), 61.32 (C-5').

Example 17

β-1'-(6-amino-9H-purin-9-yl)-3'-azido-2',3'-dideoxy-2',2'-difluororibose

A solution of 47.2 mg (0.11 mmol) α and β-1'-(6-chloro-9H-purin-9-yl)-5'-benzoyl-3'-azido-2',3'-dideoxy-2',2'-difluororibose in isopropanol (15 ml) were treated as described in Example 16. Purification yielded 11.2 mg (33%) of the title compound as a colorless solid. FAB-MS: m/e=313(M+1). $^1$H-NMR(300 MHz, $d_7$-DMF): δ8.47(s, 1H), 8.23(s, 1H), 7.50(br. s, 2H), 6.51(dd, 1H, J=5.3, 4.9 Hz), 5.64(br. s, 1H), 5.21(m, 1H), 4.21(m, 1H), 3.92(m, 2H). $^{13}$C-NMR(300 MHz, $d_7$-DMF): 157.32(C-6), 153.90(C-2), 150.20(C-4), 139.65(C-8), 124.23(C-2'), 119.81(C-5), 84.21 (C-1'), 80.50(C-4'), 60.91(C-3'), 60.80(C-5').

Example 18

α and β-1'-(4-amino-2-oxo-1H-pyrimidin-1-yl)-5'-benzoyl-3'-azido-2',3'-dideoxy-2',2'-difluororibose A solution of 127.5 mg (1.15 mmol) 4-amino-2-pyrimidone and 3.1 mg (0.02 mmol) ammonium sulfate in hexamethyldisilazane (10 ml) were stirred at reflux for 3 hours. The volatiles were removed under reduced pressure and the residue was dissolved in 1,2-dichloroethane (15 ml). To this were added 0.22 ml (1.15 mmol) trimethylsilyltrifluoromethanesulfonate and the mixture was stirred 30 minutes at room temperature at which time the cloudy solution became homogeneous. To this solution were added 290 mg (0.77 mmol) α and β-1-methanesulfonyloxy-5-benzoyl-3-azido-2,3-dideoxy-2,2-difluororibose and the mixture was stirred at reflux for 24 hours. The reaction mixture was cooled to room temperature and methanol (2 ml) added. Volatiles were removed under reduced pressure and the residue dissolved in ethyl acetate. The organic solution was washed with water, saturated aqueous sodium bicarbonate and again with water. The remaining organic phase was dried over sodium sulfate and the volatiles removed under reduced pressure. Purification by reverse phase chromatography on a $C_{18}$-column eluting with 45% acetonitrile in water at a flow rate of 6 ml/min gave 104.8 mg (35) of the title compounds as a 4:(α:D) mixture of anomers. FAB-MS: m/e=393, 394(M+1, M+2). $^1$H-NMR(300 MHz, 0.8H, α), 6.22(m, 0.2H, β), 5.99(d, 0.8H, α, J=7.5 Hz), 5.85(d, 0.2H, β, J=7, Hz), 4.50(m, 4H).

Example 19

α and β-1'-(4-amino-2-oxo-1H-pyrimidin-1-yl)-3'-azido-2',3'-dideoxy-2',2'-difluororibose A solution of 104.8 mg (0.27 mmol) α and β-1'-(4-amino-2-oxo-1H-pyrimidin-1-yl)-5'-benzoyl-3'-azido-2',3'-dideoxy-2',2'-difluororibose in methanol (25 ml) was cooled to 5° C. and gaseous ammonia was bubbled into the solution for 10 minutes. The reaction mixture was then allowed to stir at room temperature for 2½ hours. Volatiles were removed under reduced pressure to give a colorless foam. This foam was triturated with ethyl acetate to give after filtration 47.3 mg of the α-anomer of the title compound as a colorless solid. FAB-MS: m/e=289(M+1). IR: 2112.8 cm $^{-1}$, $N_3$. $^1$H-NMR(300 MHz, $d_7$-DMF): δ7.68(dd, 1H, J=2.0, 7.5 Hz), 6.54(dd, 1H, J=5.5, 12.2 Hz), 5.99(d, 1H, J=7.5 Hz), 5.54(t, 1H, J=5.8 Hz), 4.90(m, 1H), 4.44(m, 1H), 3.82(m, 2H). $^{13}$C-NMR(300 MHz, $d_7$-DMF): 167.07(C-4), 155.84(C-2), 141.83(C-6), 124.20(C-2'), 95.38(C-5), 84.68(C-1'), 82.31 (C-4'), 62.03(C-3'), 61.43(C-5').

The filtrate was concentrated under reduced pressure and the residue purified by reverse phase chromatography on a $C_{18}$ column, eluting with 24% methanol in water which contained 0.5% acetic acid at a flow rate of 10 ml/min. An additional 4.2 mg of the α-anomer and 12.6 mg of the β-anomer of the title compound were recovered. FAB-MS:

m/e=289(M+1). IR: 2117cm$^{-1}$N$_3$, $^1$H-NMR(300 MHz d$_7$-DMF): δ7.86(d 1H, J=7.5 Hz), 6.32(t, 1H, J=8.3 Hz), 5.96(d, 1H, J=7.5 Hz), 4.73(m, 1H), 4.08(m, 1H), 3.99(d, 1H, J=12.8 Hz), 3.85(dd, 1H, J=3.0, 12.8 Hz). $^{13}$C-NMR (300 MHz, d$_7$-DMF): 166.99(C-4), 155.64(C-2), 41.52(C-6), 124.60(C-2'), 95.43(C-5), 85.28(C-1'), 79.71(C-4'), 60.72(C-3'), 60.09(C-5').

A total of 69.1 mg (90%) of the title compound were recovered.

The present invention provides a method of treating susceptible neoplasms in mammals comprising administering to a mammal in need of such treatment an antineoplastically effective amount of a compound of Formula I. The method comprises administering the compound to the mammal by various routes including the oral, rectal, transdermal, subcutaneous, intravenous, intramuscular or intranasal routes.

The term "antineoplastically effective amount", as defined herein, refers to an appropriate amount of a compound of Formula I which is capable of providing chemotherapy to mammals, especially humans. The active compounds are effective over a wide dosage range. For example, dosages per day will normally fall within the range of about 0.1 to about 1200 mg/kg of body weight. In the treatment of adult humans, the range of about 0.1 to about 50 mg/kg, in single or divided doses, is preferred. However, it will be understood that the amount of compound actually administered will be determined by a physician, in the light of the relevant circumstances including the condition to be treated, the particular compound to be administered, the chosen route of administration, the age, weight, and response of the individual patient, and the severity of the patient's symptoms, and therefore the above dosage ranges are not intended to limit the scope of the invention in any way.

The term "susceptible neoplasm", as defined herein, represents an abnormal growth of tissue in mammals capable of being treated by a compound of Formula I. While the compounds of Formula I are effective against tumors, both solid and non-solid type, the compounds are effective in controlling the growth of rapidly dividing cells because of the compounds' cytotoxic nature. Examples of tumors which the compounds of Formula I would be effective against include L1210V lymphocytic leukemia, 6C3HED, CA755, P1534J, X5563 Myeloma and the like.

The antineoplastic activity of a representative compound of the present invention has been demonstrated in a standard screen commonly used by those in the art in testing compounds for potential antitumor drugs. For example, these screens have been used to demonstrate the antitumor activity of commercially available cancer drugs such as the vinca alkaloids. See, e.g., Miller et al., in *J. Med. Chem.* Vol. 20, No. 3 409 (1977) and Sweeney, et al., in *Cancer Research* 38, 2886 (1978).

The compounds of the present invention represented by Formula I are cytostatic in that they inhibit the growth of human leukemic cells (CCRF-CEM cell line). Table 1 below gives the results of such testing of compounds representative of those in Formula I. In the Table, column 1 gives the example number of the compound and column 2 the IC50 (concentration giving 50% growth inhibition) in mcg/ml.

TABLE 1

| Cytoxicity Screen | |
|---|---|
| Compound | IC$_{50}$ (mcg/ml) |
| Example 1 | 1.9 |
| Example 2 | 1.9 |
| Example 3 | 8.5 |
| Example 4 | 23.4 |
| Example 5 | >20 |
| Example 16 | 18.5 |
| Example 17 | >20 |
| Example 19 (α) | >20 |
| Example 19 (β) | >20 |

The compounds of the present method are also effective for the treatment of viral infections, and more particularly in the treatment of infections caused by viruses of the Herpes genus. As such, yet another embodiment of the present invention is a method of treating viral infections in mammals comprising administering to a mammal in need of such treatment an antivirally effective amount of a compound of Formula I.

The term "antivirally effective amount", as defined herein, refers to an appropriate amount of a compound of Formula I which is capable of preventing or inhibiting the presence of viral infections in mammals. In general, dosage rates in the range of from about 5 mg/kg to about 500 mg/kg are useful. It is more preferred to administer at rates in the range of from about 10 mg/kg to about 100 mg/kg.

The compounds defined by Formula I can be employed to treat or prevent diseases commonly caused by a wide range of viruses. Typical viruses against which the compounds of the invention can be used to control include all A and B strains of influenza, para-influenza, respiratory syncytial viruses, the various Herpes I and Herpes II strains, Echo and vaccinia viruses, measles, Semliki Forest and retroviruses such as Friends Leukemia Virus and those responsible for causing acquired immune deficiency syndrome.

The following plaque-reduction study provides a quantitative evaluation of inhibitors of virus multiplication and establishes the antiviral activity of a representative compound of the present invention.

According to this study, susceptible cells (BSC-1, Hela, MDCK, etc.) were grown in 25 cm$^2$ Falcon flasks at 37° C. in Medium 199 with 5 percent inactivated fetal bovine serum (FBS), penicillin (150 units/ml) and streptomycin (150 μg/ml). When confluent monolayers were formed, the growth medium was removed and 0.3 ml of an appropriate dilution of the virus was added to each flask. After adsorption for one hour at room temperature, the infected cell sheet was overlaid with equal parts of 1 percent AgarOse and 2×Medium 199, 2.5 percent FBS, penicillin, and streptomycin. The compound to be tested was dissolved in dimethyl sulfoxide (DMSO) at a concentration of 10,000 μg/ml and an aliquot of the resulting solution was diluted to the desired concentration with the agar medium mixture. Flasks were incubated at 37° C. until control flasks indicated optimum plaque size of about 2 to about 10 mm. A solution containing 10 percent formalin by volume and 2 percent sodium acetate by volume was added to each flask to inactivate the virus and fix the cell sheet to the plastic surface. The plaques were counted after staining the surrounding cell areas with crystal violet. Results from duplicate flasks at each concentration were averaged and compared with control flasks. The following degrees of inhibition against HSV-1 were observed.

| Compound | Concentration | Inhibition |
| --- | --- | --- |
| Ex. 1 | 15 ug/ml | 50% |
| Ex. 2 | 3.1 | 27% |
| Ex. 4 | 25 | 39% |
| Ex. 5 | 25 | 35% |
| Ex. 16 | 50 | 25% |
| Ex. 17 | 50 | 6% |
| Ex. 19(∝) | 25 | 10% |
| Ex. 19(β) | 25 | 0% |

The following degrees of inhibition against HSV-2 were observed.

| Compound | Concentration | Inhibition |
| --- | --- | --- |
| Ex. 3 | 25 ug/ml | 21% |
| Ex. 4 | 13.5 | 50% |

The following procedure was used to establish the efficacy of a representative compound of the present invention against Friends leukemia virus.

SC-1 cells from a feral mouse were seeded subconfluently at $2\text{--}5 \times 10^3$ cells per well in 96 microwell plates with complete MEM media plus 2 mcg/ml polybrene overnight at 37° C. under a carbon dioxide atmosphere. The medium was removed. The cultures were infected with a proper dilution of murine leukemia virus (50 mcl/well) and were allowed to adsorb for about two hours at room temperature. After adsorption, the virus containing medium was removed and replaced with fresh complete MEM, both with and without dilutions of the compound of Example 1, and reincubated at 37° C. under carbon dioxide for 5 days or until the cells reached confluence. The medium was removed and the cells were exposed for 10 seconds to a UV germicidal light. XC cells from a Rous sarcoma virus induced rat tumor cell line at a concentration of $5\text{--}8 \times 10^4$ cells/well were added to the irradiated SC-1 monolayers. The cultures were incubated at 37° C. under carbon dioxide for three days until CPE occurred in the control wells. Cultures were fixed with formalin and stained with crystal violet. The results were scored as CPE inhibition. The compound of Example 1 had an $IC_{50}$ of 6.5 µg/ml.

The compounds of the present invention are preferably administered as a pharmaceutical formulation. Therefore, as yet another embodiment of the present invention, a pharmaceutical formulation useful for treating susceptible neoplasms in mammals is provided comprising a compound of Formula I in combination with a pharmaceutical carrier, diluent or excipient therefor.

The active ingredient will be present in the formulation in the range of about 1% to about 90% by weight. The active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples represent specific pharmaceutical formulations employing compounds comprehended by the present method. The formulations may employ as active compounds any of the compounds of Formula I. The examples are illustrative only and are not intended to limit the scope of the invention in any way.

Formulation 1

Hard gelatin capsules are prepared using the following ingredients:

| | Quantity (mg/capsule) |
| --- | --- |
| 1-(4-amino-5-methyl-2-oxo-1H-pyrimidin-1-yl)-2,3-dideoxy-3-amino-2,2-difluororibose | 250 |
| starch dried | 200 |
| magnesium stearate | 10 |

The above ingredients are mixed and filled into hard gelatin capsules in 460 mg quantities.

Formulation 2

A tablet formula below:pared using the ingredients below:

| | Quantity (mg/tablet) |
| --- | --- |
| 1-(4-amino-2-oxo-1H-pyrimidin-1-yl)-2,3-dideoxy-2,2,3,3-tetra-fluororibose | 250 |
| cellulose, microcrystalline | 400 |
| silicon dioxide, fumed | 10 |
| stearic acid | 5 |

The components are blended and compressed to form tablets each weighing 665 mg.

Formulation 3

An aerosol solution is prepared containing the following components:

|  | Weight % |
| --- | --- |
| 1-(2,4-dioxo-1H,3H-pyrimidin-1-yl)-2,3-dideoxy-2,2-difluoro-ribose | 0.25 |
| ethanol | 29.75 |
| Propellant 22 (chlorodifluoromethane) | 70.00 |

The active compound is mixed with ethanol and the mixture added to a portion of the Propellant 22, cooled to −30° C. and transferred to a filling device. The required amount is then placed in a stainless steel container and diluted with the remainder of the propellant. The valve units are then fitted to the container.

Formulation 4

Tablets each containing 60 mg of active ingredient are made up as follows:

| 1-(4-amino-2-oxo-1H-pyrimidin-1-yl)-2,3-dideoxy-2,2-difluoro-ribose | 60 mg |
| --- | --- |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |

The difluoronucleoside, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| 1-(4-amino-2-oxo-1H-pyrimidin-1-yl)-2,3-dideoxy-3-azido-2,2-difluoroxylose | 80 mg |
| --- | --- |
| starch | 59 mg |
| microcrystalline cellulose | 59 mg |
| magnesium stearate | 2 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of difluoronucleoside are made as follows:

| 1-(2,4-dioxo-1H,3H-pyrimidin-1-yl)-2,3-dideoxy-2,2-difluoro-ribose | 225 mg |
| --- | --- |
| saturated fatty acid glycerides to | 2 g |

The nucleoside is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per ml dose are made as follows:

| 1-(4-amino-5-methyl-2-oxo-1H-pyrimidin-1-yl)-2,3-dideoxy-2,2-difluororibose | 50 mg |
| --- | --- |
| sodium carboxymethyl cellulose | 50 mg |
| syrup | 1.25 ml |
| benzoic acid solution | 0.10 ml |
| flavor | q.v. |
| color | q.v. |
| purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation is prepared as follows:

| 1-(4-amino-2-oxo-1H-pyrimidin-1-yl)-2,3-dideoxy-2,2-difluoro-ribose | 100 mg |
| --- | --- |
| isotonic saline | 1000 ml |

The solution of the above ingredients is administered intravenously at a rate of 1 ml/minute to a mammal in need of treatment from susceptible neoplasms.

We claim:

1. A compound selected from the group consisting of
   a) β-1'-(4-amino-2-oxo1H-pyrimidin-1-yl)-2',3'-dideoxy-2',2'-difluororibose, or a pharmaceutically acceptable salt thereof,
   b) β-1'-(2,6-diamino-9H-purin-9-yl)-2',3'-dideoxy-2',2'-difluororibose, or a pharmaceutically acceptable salt thereof,
   c) β-1'-(2-amino-6-oxo-9H-purin-9-yl)-2',3'-dideoxy-2',2'-fluororibose, or a pharmaceutically acceptable salt thereof,
   d) β-1'-(5-methyl-2,4-dioxo-1H,3H-pyrimidin-1-yl)-3'-azido-2',3'-dideoxy-2',2'-difluororibose, or a pharmaceutically acceptable salt thereof,
   e) β-1'-(5-methyl-2,4-dioxo-1H,3H-pyrimidin-1-yl)-2',3'-dideoxy-2',2'-difluororibose, or a pharmaceutically acceptable salt thereof,
   f) α and β-1'-(6-amino-9H-purin-9-yl)-2',3'-dideoxy-2',2'-difluororibose, or a pharmaceutically acceptable salt thereof, g) α-1'-(6-amino-9H-purin-9-yl)-3'-azido-2',3'-dideoxy-2',2'-difluororibose, or a pharmaceutically acceptable salt thereof, h) β-1'-(6-amino-9H-purin-9-yl)-3'-azido-2',3'-dideoxy-2',2'-difluororibose, or a pharmaceutically acceptable salt thereof, i) α and β-1'-(4-amino-2-oxo-1H-pyrimidin-1-yl)-3'-azido-2',3'-dideoxy-2',2'-difluororibose, or a pharmaceutically acceptable salt thereof.

2. The compound of claim 1 which is β-1-(4-amino-2-oxo-1H-pyrimidin-1-yl)-2,3-dideoxy-2,2-difluororibose or a pharmaceutically-acceptable salt thereof.

3. The compound of claim 1 which is β-1-(2,6-diamino-9H-purin-9-yl) -2,3-dideoxy-2,2-difluororibose or a pharmaceutically-acceptable salt thereof.

4. A pharmaceutical formulation comprising a compound of claim 1 and a pharmaceutically acceptable carrier, diluent or excipient therefor.

5. An intermediate selected from the group consisting of a) β-1'-[4-(2,2-dimethyl-1-oxopropylamino)-2-oxo-1H-pyrimidin-1-yl]-5'-(2,2-dimethyl-1-oxopropyloxy)-2'-deoxy-2',2'-difluororibose, b) β-1'-[4-(2,2-dimethyl-1-oxopropylamino)-2-oxo-1H-pyrimidin-1-yl]-5'-(2,2-dimethyl-1-oxopropyloxy)-3'-(O-phenylcarbonothiooxy)-2'-deoxy-2',2'-difluororibose, c) β-1'-[4-(2,2-dimethyl-1-oxopropylamino)-2-oxo-1H-pyrimidin-1-yl]-5'-(2,2-dimethyl-1-oxopropyloxy)-2',3'-dideoxy-2',2'-difluororibose, d) β-1'-(2,6-diamino-9H-purin-9-yl)-5'-benzoyl-2'-deoxy-2',2'-difluororibose, e) 1-t-butyldimethylsilyloxy-5-benzoyl-2-deoxy-2',2'-difluororibose, f) α-1'-(2,6-diamino-9H-purin-9-yl)-5'-deoxy-2',-2'-difluororibose, g) -1-t-butyldimethylsilyloxy-5-benzoyl-3-azido-2,3-dideoxy-2,2-difluororibose, h) α and β-5-benzoyl-3-azido-2,3-dideoxy-2,2-difluororibose, i) α and β-1-mesyloxy-5-benzoyl-3-azido-2,3-dideoxy-2,2-difluororibose, j) α and β-1'-(6-chloro-9H-purin-9-yl)-5'-benzoyl-2',3'-dideoxy-3'-azido-2',2'-difluororibose, and k) α and β-1'-(4-amino-2-oxo-1H-pyrimidin-1-yl)-5'-benzoyl-3'-azido-2',3'-dideoxy-2',2'-difluororibose.

* * * * *